US008017830B2

(12) United States Patent
Lightner et al.

(10) Patent No.: US 8,017,830 B2
(45) Date of Patent: Sep. 13, 2011

(54) GENERATION OF PLANTS WITH ALTERED OIL, PROTEIN OR FIBER CONTENT

(75) Inventors: Jonathan Lightner, Des Moines, IA (US); D. Ry Wagner, Pleasant Hill, OR (US)

(73) Assignee: Agrinomics, LLC, Indianapolis, IN (US)

( * ) Notice: Subject to any disclaimer, the term of this patent is extended or adjusted under 35 U.S.C. 154(b) by 475 days.

(21) Appl. No.: 12/141,830

(22) Filed: Jun. 18, 2008

(65) Prior Publication Data
US 2009/0035442 A1 Feb. 5, 2009

Related U.S. Application Data

(60) Provisional application No. 60/944,768, filed on Jun. 18, 2007.

(51) Int. Cl.
*A01H 1/00* (2006.01)
*A01H 5/10* (2006.01)
(52) U.S. Cl. ........ 800/278; 800/281; 800/298; 800/306; 800/312; 800/314; 800/320; 800/320.1; 800/320.2; 435/410; 435/468
(58) Field of Classification Search .................... None
See application file for complete search history.

(56) References Cited

U.S. PATENT DOCUMENTS

| | | | |
|---|---|---|---|
| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 2003/0046723 | A1 | 3/2003 | Heard et al. |
| 2004/0019927 | A1 | 1/2004 | Sherman et al. |
| 2004/0025202 | A1 | 2/2004 | Laurie et al. |
| 2005/0155106 | A1 | 7/2005 | Ruezinsky et al. |
| 2006/0206961 | A1 | 9/2006 | Cirpus et al. |
| 2006/0277630 | A1 | 12/2006 | Lightner et al. |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | 2004/093528 | 11/2004 |
| WO | 2004/093532 | 11/2004 |
| WO | 2005/047516 | 5/2005 |
| WO | 2005/107437 | 11/2005 |
| WO | 2007/053482 | 5/2007 |

OTHER PUBLICATIONS

Database UniProt_201006, Mar. 1, 2001.*
Bateman et al., "Pfam 3.1: 1313 multiple alignments and profile HMMs match the majority of proteins," *Nucleic Acids Res.*, 27:260-262, 1999.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).
Browse et al., "Fluxes through the prokaryotic and eukaryotic pathways of lipid synthesis in the '16:3' plant *Arabidopsis thaliana*," *Biochem J.* 235:25-31 (1986).
Chapple and Carpita, "Plant cell walls as targets for biotechnology," *Current Opinion in Plant Biology*, 1:179-185 (1998).
Christensen et al., *9th International Conference on Arabidopsis Research*, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
Colbert et al., "High-throughput screening for induced point mutations," *Plant Physiol.* 126:480-484 (2001).
De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).
Douglas et al., "Nutritional evaluation of low phytate and high protein corns," *Poultry Sci.* 79:1586-1591 (2000).
Edwards et al., "Protein and energy evaluation of soybean meals processed from genetically modified high-protein soybeans," *Poultry Sci.* 79:525-527 (1999).
Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).
Feldmann et al., "A Dwarf Mutant of Arabidopsis Generated by T-DNA Insertion Mutagenesis," *Science*, 243:1351-1354 (1989).
Focks and Benning, "wrinkled1: A novel, low-seed-oil mutant of Arabidopsis with a deficiency in the seed-specific regulation of carbohydrate metabolism," *Plant Physiol.*, 118:91-101 (1998).
Fridborg et al., "The Arabidopsis dwarf mutant *shi* exhibits reduced gibberellin responses conferred by overexpression of a new putative zinc finger protein," *Plant Cell*, 11:1019-1032 (1999).
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem.*, 27:1262-1266 (1979).
Jako et al., "Seed-specific over-expression of an Arabidopsis cDNA encoding a diacylglycerol acyltransferase enhances seed oil content and seed weight," *Plant Physiol.*, 126(2):861-74 (2001).
James and Dooner, "Isolation of EMS-induced mutants in Arabidopsis altered in seed fatty acid composition," *Theor. Appl. Genet.*, 80:241-245 (1990).

(Continued)

*Primary Examiner* — Eileen B O'Hara
(74) *Attorney, Agent, or Firm* — Klarquist Sparkman, LLP.

(57) ABSTRACT

The present invention is directed to plants that display an improved oil quantity phenotype or an improved meal quality phenotype due to altered expression of an HIO nucleic acid. The invention is further directed to methods of generating plants with an improved oil quantity phenotype or improved meal quality phenotype.

21 Claims, No Drawings

OTHER PUBLICATIONS

Kardailsky et al., "Activation tagging of the floral inducer FT," *Science*, 286:1962-1965 (1999).

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).

Klein et al., "High velocity microprojectiles for delivering nucleic acids into living cells," *Nature*, 327:70-73 (1987).

Lemieux et al., "Mutants of Arabidopsis with alterations in seed lipid fatty acid composition," *Theor. Appl. Genet.*, 80:234-240 (1990).

Lionneton et al., "Development of an AFLP-based linkage map and localization of QTLs for seed fatty acid content in condiment mustard (*Brassica juncea*)," *Genome*, 45:1203-15 (2002).

McCallum et al., "Targeted screening for induced mutations," *Nature Biotechnology*, 18:455-457 (2000).

Moore et al., "Chromatography of Amino Acids on Sulfonated Polystyrene Resins," *Anal. Chem.*, 30:1185-1190 (1958).

Mulder et al., "The InterPro Database, 2003 brings increased coverage and new features," *Nucleic Acids Res.*, 31:315-318, 2003.

Okuley et al., "Arabidopsis *FAD2* gene encodes the enzyme that is essential for polyunsaturated lipid synthesis," *Plant Cell*, 6:147-158 (1994).

Parsons et al., "Nutritional evaluation of soybean meals varying in oligosaccharide content," *Poultry Sci.*, 79:1127-1131 (2000).

Schaffer et al., "The late elongated hypocotyl mutation of Arabidopsis disrupts circadian rhythms and the photoperiodic control of flowering," *Cell*, 93:1219-1229 (1998).

Shewry, "Seed storage proteins: structures and biosynthesis," *Plant Cell*, 7:945-956 (1995).

Weigel et al., "Activation tagging in Arabidopsis," *Plant Physiology*, 122:1003-1013 (2000).

Wilson et al., "A Dissociation insertion causes a semidominant mutation that increases expression of TINY, an Arabidopsis gene related to APETALA2," *Plant Cell*, 8:659-671 (1996).

Yadav et al., "Cloning of higher plant omega-3 fatty acid desaturases," *Plant Physiol.*, 103:467-476 (1993).

\* cited by examiner

SEQUENCE LISTING

<160> NUMBER OF SEQ ID NOS: 8

<210> SEQ ID NO 1
<211> LENGTH: 381
<212> TYPE: DNA
<213> ORGANISM: Arabidopsis thaliana

<400> SEQUENCE: 1

```
atgtctgcag ttcaactcga tttgcaagac agatgggtct taaaaatgta tggatggatg      60
aacaagaacg ttaagtggat tgcccaact  gctcctagac gccccttac  tatcctaggt     120
ggaatggaaa ccaatgcatg gttcgatatc gcagaacttt ctgaaaacat gcaagatgat     180
gtggcgtcat taaatcatgc tgctttatct attgctaacc ttttatctga agaacccaca     240
aacggaatag gaggtatcgg ctttggtgca gcgcaagctc tctaccttgc gagtaagggt     300
tgttatgaca ctaatcaacg gcttcaaata aagccacgag ttgttatagg gctcaatggt     360
tggcttcctg tctggaggta g                                                381
```

<210> SEQ ID NO 2
<211> LENGTH: 126
<212> TYPE: PRT
<213> ORGANISM: Arabidopsis thaliana

<400> SEQUENCE: 2

```
Met Ser Ala Val Gln Leu Asp Leu Gln Asp Arg Trp Val Leu Lys Met
1               5                   10                  15

Tyr Gly Trp Met Asn Lys Asn Val Lys Trp Ile Cys Pro Thr Ala Pro
                20                  25                  30

Arg Arg Pro Leu Thr Ile Leu Gly Gly Met Glu Thr Asn Ala Trp Phe
            35                  40                  45

Asp Ile Ala Glu Leu Ser Glu Asn Met Gln Asp Val Ala Ser Leu
        50                  55                  60

Asn His Ala Ala Leu Ser Ile Ala Asn Leu Leu Ser Glu Glu Pro Thr
65                  70                  75                  80

Asn Gly Ile Gly Gly Ile Gly Phe Gly Ala Ala Gln Ala Leu Tyr Leu
                85                  90                  95

Ala Ser Lys Gly Cys Tyr Asp Thr Asn Gln Arg Leu Gln Ile Lys Pro
            100                 105                 110

Arg Val Val Ile Gly Leu Asn Gly Trp Leu Pro Val Trp Arg
        115                 120                 125
```

<210> SEQ ID NO 3
<211> LENGTH: 561
<212> TYPE: DNA
<213> ORGANISM: Arabidopsis thaliana

<400> SEQUENCE: 3

```
atgtttcttg catactttc aaagttgttg gactatattc tctcctatat ttattacgtg      60
gaactgatta atgaatctgc gtatgttaaa cttttacag ctcgtagaaa tgtaggggt      120
attaaatttg aagacgttca atcttttgga cccataggaa ctcataaggc cactatagtc   180
tggctgcatg atatcggcga gacaagcgca aattcggttc gatttgcgag acagttgggt   240
cttcgaaata ttaagtggat tgtccaact gctcctagac gccccgttac tatcttaggt    300
ggaatggaaa ccaatgcatg gttcgatatt gcagaaattt ctgaaaacat gcaagatgat   360
gaggtgtcat tacatcatgc agctttatct attgctaacc ttttttctga tcatgcttcc   420
ccaaatatag gaggtatggg catgggtgca gcgcaagctc tctaccttgc gagtaagagt   480
tgctatgaca ctaatcaacg gcttcaaata aagccacgag ttgttatagg gcttaaagga   540
tggcttcctg gctggaggta g                                             561
```

<210> SEQ ID NO 4
<211> LENGTH: 186
<212> TYPE: PRT
<213> ORGANISM: Arabidopsis thaliana

<400> SEQUENCE: 4

```
Met Phe Leu Ala Tyr Phe Ser Lys Leu Leu Asp Tyr Ile Leu Ser Tyr
1               5                   10                  15
Ile Tyr Tyr Val Glu Leu Ile Asn Glu Ser Ala Tyr Val Lys Leu Phe
                20                  25                  30
Thr Ala Arg Arg Asn Val Gly Gly Ile Lys Phe Glu Asp Val Gln Ser
            35                  40                  45
Phe Gly Pro Ile Gly Thr His Lys Ala Thr Ile Val Trp Leu His Asp
        50                  55                  60
Ile Gly Glu Thr Ser Ala Asn Ser Val Arg Phe Ala Arg Gln Leu Gly
65                  70                  75                  80
Leu Arg Asn Ile Lys Trp Ile Cys Pro Thr Ala Pro Arg Arg Pro Val
                85                  90                  95
Thr Ile Leu Gly Gly Met Glu Thr Asn Ala Trp Phe Asp Ile Ala Glu
                100                 105                 110
Ile Ser Glu Asn Met Gln Asp Asp Glu Val Ser Leu His His Ala Ala
            115                 120                 125
Leu Ser Ile Ala Asn Leu Phe Ser Asp His Ala Ser Pro Asn Ile Gly
        130                 135                 140
Gly Met Gly Met Gly Ala Ala Gln Ala Leu Tyr Leu Ala Ser Lys Ser
145                 150                 155                 160
Cys Tyr Asp Thr Asn Gln Arg Leu Gln Ile Lys Pro Arg Val Val Ile
                165                 170                 175
Gly Leu Lys Gly Trp Leu Pro Gly Trp Arg
                180                 185
```

<210> SEQ ID NO 5
<211> LENGTH: 2606
<212> TYPE: DNA
<213> ORGANISM: Arabidopsis thaliana

<400> SEQUENCE: 5

```
aattttcat tgttcttgat gaaactgagg ccacgacgaa tcgcaaatgg aggcgatcaa      60
accacttcca caggtctcga gcttctccgc ttcggtattt agctttctcg atggcagatt   120
caaagaatcc acggatctct ctcattctac gggtctggtt tccgagttac agacggagat   180
```

```
ttccgaattg gatcagagat tggccggatt aaatcgccag ctcgagtcag gtctcgctgc    240
ttacgcttcg ttttccgatc gcgtcggtgg tctattttc gaggttaatg ccaaattggc     300
tgatctctct tcttctacct ccgttactcg ctccgcgtca gatagcgaa aggaggagga     360
ggcgacggag catgtagccg gagaggatct tccttcatta gcaaaggaag tagcacaagt    420
tgagtctgtg cgtgcttatg ctgagactgc actaaaactt gacactttag ttggtgatat    480
tgaggatgct gtgatgtctt ctttgaataa aaacttaaga acatctcggt caagtggttt    540
tgaagaagtg cgtctacatg ctattaaaac acttaaaacg acagaagaga tactgagttc    600
agtagcaaag agacatcctc ggtgggcacg tcttgtttct gctgttgatc atagagttga    660
tagagcttta gctatgatga gacctcaggc aattgctgat tacagagcgt tgctttcttc    720
tcttcgatgg ccacctcagc tttctacact aacttcggca agtcttgatt caaagtcaga    780
aaatgttcaa aatccgcttt tcaacatgga agggagcctc aaaagtcaat actgtggaag    840
ttttcatgcc ttgtgtagcc tgcaggggtt acagttgcaa agaaagtcgc ggcagcttgg    900
gatccataag ggagaaaatg ttcttttcca ccagccactc tgggctattg aagagctggt    960
caaccctctg acagttgcat ctcagcgaca ttttacaaag tggagtgaaa agccagaatt    1020
cattttgcc cttgtgtata aaatcacaag ggactatgtc gattctatgg atgagttgtt     1080
acaaccgctt gtggatgaag caaaactagc tgggtacagt tgccgagaag agtgggtttc    1140
ggctatggta agctcactgt ctttgtactt ggtgaaagag atctttccta tatatgttgg    1200
tcagctagac gaagcaaatg aaactgatct tcgttctgag gctaaggtct cgtggctcca    1260
tctcattgac ctgatgatct cctttgataa gcgagttcag tctttggtat cacaatcagg    1320
aatactttcg cttcaagaag atgggaatct tttgagaatt tcctctctct cagttttctg    1380
tgacagacct gattggcttg atttatgggc agagatagag ctagatgaga ggctcgtcaa    1440
attcaaggag gagattgata cgacagaaa ttggacagcg aaggtccaag acgaactcat      1500
ctccagttcc aacgtttaca gaccaccaat catttccagc atctttctac agcatttgtc    1560
atcaataatc gaacgatcca aatcagtgcc ggccttatat ttgagggcta ggttcctgag    1620
actggcagcc tcaccaacaa ttcataagtt cttggattgc ctccttctca ggtgccaaga    1680
cgccgacgga ctaactgcat taactgaaaa taacgatcta atcaaggtct cgaactctat    1740
taatgctggt cactacattg aatctgtctt agaagaatgg tctgaggatg tcttttttcct  1800
tgaaatggga actggacagc acgatccaca ggaagttcca ggactggaga actttactga    1860
accttctgaa ggtattttcg gagaagaatt tgaaaagttg gagaagttcc ggctagagtg    1920
gataaacaaa ttgtcggtgg tgatcttgag aggctttgat gctcgaatcc gagaatacat    1980
aaaaaacaga aagcaatggc aggagaagaa agacaaagaa tggacggtgt caagggcact    2040
agttggggct ctagactact tgcaaggaaa aacgtctata atagaagaaa atctaaacaa    2100
agcagacttt accgctatgt ggagaactct agcctcagag atagacaagt tgttcttcaa    2160
cagcatcttg atggcgaacg tgaagtttac caatgatgga gtcgaaaggt taaaagtaga    2220
catggaggtt ctatatgggg ttttccggac gtggtgtgtt agacccgaag gtttctttcc    2280
taaactaagt gaggggctta cgcttctgaa gatggaagag aagcaagtga aggacggtct    2340
gagtagaggc gataagtggc tacgtgagaa tagaattcga tatttgagtg aagccgaagc    2400
caagaaggta gcgaagagta gagtgttctc ttagttagat attttcagc aaatcaatat     2460
ctcatacgaa ggtacattca taggtgagat catttcattt atttgtggat taagatataa    2520
cacacaactt tggattttta attgaaattg aactaaccag ctctggttct gtttcgtctt    2580
```

```
aaattaatga ttcatgagtt aataga                                        2606
```

<210> SEQ ID NO 6
<211> LENGTH: 795
<212> TYPE: PRT
<213> ORGANISM: Arabidopsis thaliana

<400> SEQUENCE: 6

| | | | | | | | | | | | | | | | |
|---|---|---|---|---|---|---|---|---|---|---|---|---|---|---|---|
| Met | Glu | Ala | Ile | Lys | Pro | Leu | Pro | Gln | Val | Ser | Ser | Phe | Ser | Ala | Ser |
| 1 | | | | 5 | | | | | 10 | | | | | 15 | |
| Val | Phe | Ser | Phe | Leu | Asp | Gly | Arg | Phe | Lys | Glu | Ser | Thr | Asp | Leu | Ser |
| | | | 20 | | | | | 25 | | | | | 30 | | |
| His | Ser | Thr | Gly | Leu | Val | Ser | Glu | Leu | Gln | Thr | Glu | Ile | Ser | Glu | Leu |
| | | | 35 | | | | | 40 | | | | | 45 | | |
| Asp | Gln | Arg | Leu | Ala | Gly | Leu | Asn | Arg | Gln | Leu | Glu | Ser | Gly | Leu | Ala |
| | | 50 | | | | | 55 | | | | | 60 | | | |
| Ala | Tyr | Ala | Ser | Phe | Ser | Asp | Arg | Val | Gly | Gly | Leu | Phe | Phe | Glu | Val |
| 65 | | | | | 70 | | | | | 75 | | | | | 80 |
| Asn | Ala | Lys | Leu | Ala | Asp | Leu | Ser | Ser | Ser | Thr | Ser | Val | Thr | Arg | Ser |
| | | | | 85 | | | | | 90 | | | | | 95 | |
| Ala | Ser | Asp | Ser | Gly | Lys | Glu | Glu | Ala | Thr | Glu | His | Val | Ala | Gly |
| | | | 100 | | | | | 105 | | | | | 110 | | |
| Glu | Asp | Leu | Pro | Ser | Leu | Ala | Lys | Glu | Val | Ala | Gln | Val | Glu | Ser | Val |
| | | | 115 | | | | | 120 | | | | | 125 | | |
| Arg | Ala | Tyr | Ala | Glu | Thr | Ala | Leu | Lys | Leu | Asp | Thr | Leu | Val | Gly | Asp |
| | | 130 | | | | | 135 | | | | | 140 | | | |
| Ile | Glu | Asp | Ala | Val | Met | Ser | Ser | Leu | Asn | Lys | Asn | Leu | Arg | Thr | Ser |
| 145 | | | | | 150 | | | | | 155 | | | | | 160 |
| Arg | Ser | Ser | Gly | Phe | Glu | Glu | Val | Arg | Leu | His | Ala | Ile | Lys | Thr | Leu |
| | | | | 165 | | | | | 170 | | | | | 175 | |
| Lys | Thr | Thr | Glu | Glu | Ile | Leu | Ser | Ser | Val | Ala | Lys | Arg | His | Pro | Arg |
| | | | 180 | | | | | 185 | | | | | 190 | | |
| Trp | Ala | Arg | Leu | Val | Ser | Ala | Val | Asp | His | Arg | Val | Asp | Arg | Ala | Leu |
| | | | 195 | | | | | 200 | | | | | 205 | | |
| Ala | Met | Met | Arg | Pro | Gln | Ala | Ile | Ala | Asp | Tyr | Arg | Ala | Leu | Leu | Ser |
| | | 210 | | | | | 215 | | | | | 220 | | | |
| Ser | Leu | Arg | Trp | Pro | Pro | Gln | Leu | Ser | Thr | Leu | Thr | Ser | Ala | Ser | Leu |
| 225 | | | | | 230 | | | | | 235 | | | | | 240 |
| Asp | Ser | Lys | Ser | Glu | Asn | Val | Gln | Asn | Pro | Leu | Phe | Asn | Met | Glu | Gly |
| | | | | 245 | | | | | 250 | | | | | 255 | |
| Ser | Leu | Lys | Ser | Gln | Tyr | Cys | Gly | Ser | Phe | His | Ala | Leu | Cys | Ser | Leu |
| | | | 260 | | | | | 265 | | | | | 270 | | |
| Gln | Gly | Leu | Gln | Leu | Gln | Arg | Lys | Ser | Arg | Gln | Leu | Gly | Ile | His | Lys |
| | | | 275 | | | | | 280 | | | | | 285 | | |
| Gly | Glu | Asn | Val | Leu | Phe | His | Gln | Pro | Leu | Trp | Ala | Ile | Glu | Glu | Leu |
| | | 290 | | | | | 295 | | | | | 300 | | | |
| Val | Asn | Pro | Leu | Thr | Val | Ala | Ser | Gln | Arg | His | Phe | Thr | Lys | Trp | Ser |
| 305 | | | | | 310 | | | | | 315 | | | | | 320 |
| Glu | Lys | Pro | Glu | Phe | Ile | Phe | Ala | Leu | Val | Tyr | Lys | Ile | Thr | Arg | Asp |
| | | | | 325 | | | | | 330 | | | | | 335 | |
| Tyr | Val | Asp | Ser | Met | Asp | Glu | Leu | Leu | Gln | Pro | Leu | Val | Asp | Glu | Ala |
| | | | 340 | | | | | 345 | | | | | 350 | | |
| Lys | Leu | Ala | Gly | Tyr | Ser | Cys | Arg | Glu | Glu | Trp | Val | Ser | Ala | Met | Val |
| | | | 355 | | | | | 360 | | | | | 365 | | |

```
Ser Ser Leu Ser Leu Tyr Leu Val Lys Glu Ile Phe Pro Ile Tyr Val
    370                 375                 380

Gly Gln Leu Asp Glu Ala Asn Glu Thr Asp Leu Arg Ser Glu Ala Lys
385                 390                 395                 400

Val Ser Trp Leu His Leu Ile Asp Leu Met Ile Ser Phe Asp Lys Arg
                405                 410                 415

Val Gln Ser Leu Val Ser Gln Ser Gly Ile Leu Ser Leu Gln Glu Asp
            420                 425                 430

Gly Asn Leu Leu Arg Ile Ser Ser Leu Ser Val Phe Cys Asp Arg Pro
        435                 440                 445

Asp Trp Leu Asp Leu Trp Ala Glu Ile Glu Leu Asp Glu Arg Leu Val
    450                 455                 460

Lys Phe Lys Glu Glu Ile Asp Asn Asp Arg Asn Trp Thr Ala Lys Val
465                 470                 475                 480

Gln Asp Glu Leu Ile Ser Ser Ser Asn Val Tyr Arg Pro Pro Ile Ile
                485                 490                 495

Ser Ser Ile Phe Leu Gln His Leu Ser Ser Ile Ile Glu Arg Ser Lys
            500                 505                 510

Ser Val Pro Ala Leu Tyr Leu Arg Ala Arg Phe Leu Arg Leu Ala Ala
        515                 520                 525

Ser Pro Thr Ile His Lys Phe Leu Asp Cys Leu Leu Leu Arg Cys Gln
    530                 535                 540

Asp Ala Asp Gly Leu Thr Ala Leu Thr Glu Asn Asn Asp Leu Ile Lys
545                 550                 555                 560

Val Ser Asn Ser Ile Asn Ala Gly His Tyr Ile Glu Ser Val Leu Glu
                565                 570                 575

Glu Trp Ser Glu Asp Val Phe Phe Leu Glu Met Gly Thr Gly Gln His
            580                 585                 590

Asp Pro Gln Glu Val Pro Gly Leu Glu Asn Phe Thr Glu Pro Ser Glu
        595                 600                 605

Gly Ile Phe Gly Glu Glu Phe Glu Lys Leu Glu Lys Phe Arg Leu Glu
    610                 615                 620

Trp Ile Asn Lys Leu Ser Val Val Ile Leu Arg Gly Phe Asp Ala Arg
625                 630                 635                 640

Ile Arg Glu Tyr Ile Lys Asn Arg Lys Gln Trp Gln Glu Lys Lys Asp
                645                 650                 655

Lys Glu Trp Thr Val Ser Arg Ala Leu Val Gly Ala Leu Asp Tyr Leu
            660                 665                 670

Gln Gly Lys Thr Ser Ile Ile Glu Glu Asn Leu Asn Lys Ala Asp Phe
        675                 680                 685

Thr Ala Met Trp Arg Thr Leu Ala Ser Glu Ile Asp Lys Leu Phe Phe
    690                 695                 700

Asn Ser Ile Leu Met Ala Asn Val Lys Phe Thr Asn Asp Gly Val Glu
705                 710                 715                 720

Arg Leu Lys Val Asp Met Glu Val Leu Tyr Gly Val Phe Arg Thr Trp
                725                 730                 735

Cys Val Arg Pro Glu Gly Phe Phe Pro Lys Leu Ser Glu Gly Leu Thr
            740                 745                 750

Leu Leu Lys Met Glu Glu Lys Gln Val Lys Asp Gly Leu Ser Arg Gly
        755                 760                 765

Asp Lys Trp Leu Arg Glu Asn Arg Ile Arg Tyr Leu Ser Glu Ala Glu
    770                 775                 780

Ala Lys Lys Val Ala Lys Ser Arg Val Phe Ser
785                 790                 795
```

<210> SEQ ID NO 7
<211> LENGTH: 2463
<212> TYPE: DNA
<213> ORGANISM: Arabidopsis thaliana

<400> SEQUENCE: 7

| | | | | | |
|---|---|---|---|---|---|
| aaacaaaagg | aacaaccttt | ttcccggcaa | atgcttccga | tggaacatcc | acttccactg | 60 |
| tcgttcgtct | tgccaaaccc | ggccacccTt | cccggtctcg | cactaggctt | tattgacggt | 120 |
| aatttcgtag | acctccaaga | tctgctcctc | cgcgcttcga | ctctgacgtc | caatttaaac | 180 |
| cacgactgtt | ctgatctaaa | cgaccgtctt | ctccatctcc | ggacggatct | cacgaagcac | 240 |
| gccgtttcct | ggatctcaac | ctcactttcc | gctaaagttt | cactcgaaga | tttgagattg | 300 |
| aacctggaga | gcctcctctg | tctccctacg | gattctgtcg | gaaagcaaac | gaattgggag | 360 |
| ttacagcaag | tcgtagagga | attgtgtcgt | atacagaatc | ggcgtaaata | tttcgtgact | 420 |
| gccttaaagt | tggaaagtct | tgttggcgat | cttgaagatt | ctgtgtttca | tccgataagt | 480 |
| aaacgcaaag | gaagtacgct | tcaagatctt | gcattgaagc | aagagagatt | cagtcatgct | 540 |
| attaagacca | tgaatgagat | tgaagaaata | cttggtgatg | ttacaaggca | tcactcacgg | 600 |
| tggcgtcgcc | ttgtagattc | tgttgatagt | agagtagata | aaagtctgtc | tgttcttcgt | 660 |
| ccacagatta | tcgcagatca | ccgagctttt | ctctcatctc | ttggctggcc | accaaaactt | 720 |
| gcaacatcca | aagtcgagca | tggagaggtt | gatagtatcc | ctaatcctct | actcttgatg | 780 |
| caaggagata | aaaagagtc | ttattcccaa | agctttctac | tcctctgtgg | tttacagcaa | 840 |
| cataatacgc | agaaggaaaa | acgaagaag | cttaatatga | ccaaagaaac | tgataatgat | 900 |
| ggactttggg | cgaccgatga | actagttaaa | ccggttgcat | ctcggatgga | gtatcatttt | 960 |
| ctaaaatggg | ctgagcaacc | tgagtttatt | tttgaacttg | tctataaagt | tacaagagac | 1020 |
| tttgctgatg | gggttgacga | tttcttacag | cctttgattg | atagggctat | gttagtaagc | 1080 |
| tgtagtgcta | agaagcttg | ggtttcagcg | atggccaaa | tgctatctgg | tttcttagag | 1140 |
| aaaaaagttt | ttcctgggct | tatagatatg | tacaaggaga | agcacatgaa | atctgaaggt | 1200 |
| atttcatcgt | ggttccatct | tgtcgatcag | atggttacat | ttgataagcg | aatgcagtct | 1260 |
| tttgtgaata | cagatacttg | tctatcttat | gaaggctctt | cgacagcgtt | ttctcaaggt | 1320 |
| atatcagtaa | tgggactgtt | ttgtaagaaa | cctgagtggc | tcaaaacctg | ggggaagatt | 1380 |
| gagctaaagg | atgcttatag | aaaaagtaaa | gaggatatta | agaatgagaa | agcttgggta | 1440 |
| attgatagtg | aaagaactag | acttggtaat | gaatccaact | cacagtctgc | aaagtatgtt | 1500 |
| ctatctacaa | gagaagatta | taaagcgcca | ttagtagcag | actcttttct | taataggact | 1560 |
| tggaggttga | tagaccatgg | tctatctcta | ccggccattc | taccaaggat | ccaatttata | 1620 |
| agagctactg | ccaccagatt | tctctggtgt | atattcaaaa | ttctgttatt | ggagttcaaa | 1680 |
| aagactgatc | tctctcatta | tggtttgtct | gaagatacac | tgatacaagc | atgtggaccg | 1740 |
| gttaatgctg | ctcggtatct | tgaatcaaaa | ctacgagaat | ggagtgatga | tttggttttt | 1800 |
| gtagagatgt | gggctgccga | aaccagtgtc | aaagttgata | gaaaacctga | agtttcctgc | 1860 |
| caaggctgct | ttttggggga | agaactgaaa | agccttgttg | agttggaaac | caattggctt | 1920 |
| atggagatta | taacagtttt | tctccaccaa | tttgacaatc | tttgcagcga | ccacttccac | 1980 |
| aacaatgcag | tttcatggga | cgaagacgtc | attaccagct | ccagcaattt | aacagtgtct | 2040 |
| cagggtgtcg | cagaagcatt | ggacaattta | agaaggcatc | tgtgtgttct | tcatctaaac | 2100 |
| atgaacccga | aagacttctt | ggacttgtgg | agaaatctcg | cggaagggct | tgaccattat | 2160 |

```
gtttctcgta aatttttctc aggagaacct gttttacgga gacaaaagtt tgataggttt    2220
gaagttgacg cagaggcact tcttactgtg cttaaacctt attgtgttcg tcctggtgca    2280
tttttccctc gtgtgcgaga gattcttagg ctgttgagga tgcatgagga agaaaaggca    2340
cgattgagag gagctctaag tcgaagtgga aatacttgtc taaagttgtt tggtatttct    2400
aacttgtctc ctcaacttgt ggaacaattt tgtaggtctt actagtaatg aatgccttt     2460 tgt                                                                  2463
```

<210> SEQ ID NO 8
<211> LENGTH: 804
<212> TYPE: PRT
<213> ORGANISM: Arabidopsis thaliana

<400> SEQUENCE: 8

```
Met Leu Pro Met Glu His Pro Leu Pro Leu Ser Phe Val Leu Pro Asn
1               5                   10                  15

Pro Ala Thr Leu Pro Gly Leu Ala Leu Gly Phe Ile Asp Gly Asn Phe
            20                  25                  30

Val Asp Leu Gln Asp Leu Leu Leu Arg Ala Ser Thr Leu Thr Ser Asn
        35                  40                  45

Leu Asn His Asp Cys Ser Asp Leu Asn Asp Arg Leu Leu His Leu Arg
    50                  55                  60

Thr Asp Leu Thr Lys His Ala Val Ser Trp Ile Ser Thr Ser Leu Ser
65                  70                  75                  80

Ala Lys Val Ser Leu Glu Asp Leu Arg Leu Asn Leu Glu Ser Leu Leu
                85                  90                  95

Cys Leu Pro Thr Asp Ser Val Gly Lys Gln Thr Asn Trp Glu Leu Gln
            100                 105                 110

Gln Val Val Glu Glu Leu Cys Arg Ile Gln Asn Arg Arg Lys Tyr Phe
        115                 120                 125

Val Thr Ala Leu Lys Leu Glu Ser Leu Val Gly Asp Leu Glu Asp Ser
    130                 135                 140

Val Phe His Pro Ile Ser Lys Arg Lys Gly Ser Thr Leu Gln Asp Leu
145                 150                 155                 160

Ala Leu Lys Gln Glu Arg Phe Ser His Ala Ile Lys Thr Met Asn Glu
                165                 170                 175

Ile Glu Glu Ile Leu Gly Asp Val Thr Arg His His Ser Arg Trp Arg
            180                 185                 190

Arg Leu Val Asp Ser Val Asp Ser Arg Val Asp Lys Ser Leu Ser Val
        195                 200                 205

Leu Arg Pro Gln Ile Ile Ala Asp His Arg Ala Phe Leu Ser Ser Leu
    210                 215                 220

Gly Trp Pro Pro Lys Leu Ala Thr Ser Lys Val Glu His Gly Glu Val
225                 230                 235                 240

Asp Ser Ile Pro Asn Pro Leu Leu Met Gln Gly Asp Lys Lys Glu
                245                 250                 255

Ser Tyr Ser Gln Ser Phe Leu Leu Cys Gly Leu Gln Gln His Asn
            260                 265                 270

Thr Gln Lys Glu Lys Arg Lys Lys Leu Asn Met Thr Lys Glu Thr Asp
        275                 280                 285

Asn Asp Gly Leu Trp Ala Thr Asp Glu Leu Val Lys Pro Val Ala Ser
    290                 295                 300

Arg Met Glu Tyr His Phe Leu Lys Trp Ala Glu Gln Pro Glu Phe Ile
305                 310                 315                 320
```

```
Phe Glu Leu Val Tyr Lys Val Thr Arg Asp Phe Ala Asp Gly Val Asp
                325                 330                 335

Asp Phe Leu Gln Pro Leu Ile Asp Arg Ala Met Leu Val Ser Cys Ser
            340                 345                 350

Ala Lys Glu Ala Trp Val Ser Ala Met Val Gln Met Leu Ser Gly Phe
        355                 360                 365

Leu Glu Lys Lys Val Phe Pro Gly Leu Ile Asp Met Tyr Lys Glu Lys
    370                 375                 380

His Met Lys Ser Glu Gly Ile Ser Ser Trp Phe His Leu Val Asp Gln
385                 390                 395                 400

Met Val Thr Phe Asp Lys Arg Met Gln Ser Phe Val Asn Thr Asp Thr
                405                 410                 415

Cys Leu Ser Tyr Glu Gly Ser Ser Thr Ala Phe Ser Gln Gly Ile Ser
            420                 425                 430

Val Met Gly Leu Phe Cys Lys Lys Pro Glu Trp Leu Lys Thr Trp Gly
        435                 440                 445

Lys Ile Glu Leu Lys Asp Ala Tyr Arg Lys Ser Lys Glu Asp Ile Lys
    450                 455                 460

Asn Glu Lys Ala Trp Val Ile Asp Ser Glu Arg Thr Arg Leu Gly Asn
465                 470                 475                 480

Glu Ser Asn Ser Gln Ser Ala Lys Tyr Val Leu Ser Thr Arg Glu Asp
                485                 490                 495

Tyr Lys Ala Pro Leu Val Ala Asp Ser Phe Leu Asn Arg Thr Trp Arg
            500                 505                 510

Leu Ile Asp His Gly Leu Ser Leu Pro Ala Ile Leu Pro Arg Ile Gln
    515                 520                 525

Phe Ile Arg Ala Thr Ala Thr Arg Phe Leu Trp Cys Ile Phe Lys Ile
    530                 535                 540

Leu Leu Leu Glu Phe Lys Lys Thr Asp Leu Ser His Tyr Gly Leu Ser
545                 550                 555                 560

Glu Asp Thr Leu Ile Gln Ala Cys Gly Pro Val Asn Ala Ala Arg Tyr
                565                 570                 575

Leu Glu Ser Lys Leu Arg Glu Trp Ser Asp Asp Leu Val Phe Val Glu
            580                 585                 590

Met Trp Ala Ala Glu Thr Ser Val Lys Val Asp Arg Lys Pro Glu Val
        595                 600                 605

Ser Cys Gln Gly Cys Phe Phe Gly Glu Glu Leu Lys Ser Leu Val Glu
    610                 615                 620

Leu Glu Thr Asn Trp Leu Met Glu Ile Ile Thr Val Phe Leu His Gln
625                 630                 635                 640

Phe Asp Asn Leu Cys Ser Asp His Phe His Asn Ala Val Ser Trp
                645                 650                 655

Asp Glu Asp Val Ile Thr Ser Ser Asn Leu Thr Val Ser Gln Gly
            660                 665                 670

Val Ala Glu Ala Leu Asp Asn Leu Arg Arg His Leu Cys Val Leu His
    675                 680                 685

Leu Asn Met Asn Pro Lys Asp Phe Leu Asp Leu Trp Arg Asn Leu Ala
    690                 695                 700

Glu Gly Leu Asp His Tyr Val Ser Arg Lys Phe Phe Ser Gly Glu Pro
705                 710                 715                 720

Val Leu Arg Arg Gln Lys Phe Asp Arg Phe Glu Val Asp Ala Glu Ala
                725                 730                 735

Leu Leu Thr Val Leu Lys Pro Tyr Cys Val Arg Pro Gly Ala Phe Phe
```

```
            740                 745                 750
Pro Arg Val Arg Glu Ile Leu Arg Leu Leu Arg Met His Glu Glu Glu
            755                 760                 765

Lys Ala Arg Leu Arg Gly Ala Leu Ser Arg Ser Gly Asn Thr Cys Leu
    770                 775                 780

Lys Leu Phe Gly Ile Ser Asn Leu Ser Pro Gln Leu Val Glu Gln Phe
785                 790                 795                 800

Cys Arg Ser Tyr
```

GENERATION OF PLANTS WITH ALTERED OIL, PROTEIN OR FIBER CONTENT

CROSS REFERENCE TO RELATED APPLICATION(S)

This application claims the benefit of U.S. Provisional Application No. 60/944,768, filed Jun. 18, 2007, the entirety of which is incorporated herein by reference.

FIELD OF THE DISCLOSURE

The present disclosure is related to transgenic plants with altered oil, protein, and/or fiber content, as well as methods of making plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the $10^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has not been able to achieve seed oil content above 9%. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 Bio/Technology 13:577-582) increases the availability of this essential amino acid and decreases the need for nutritional supplements. Soybean varieties with increased seed protein were shown to contain considerably more metabolizable energy than conventional varieties (Edwards et al., 1999, Poultry Sci. 79:525-527). Decreasing the phytate content of corn seed has been shown to increase the bioavailability of amino acids in animal feeds (Douglas et al., 2000, Poultry Sci. 79:1586-1591) and decreasing oligosaccharide content in soybean meal increases the metabolizable energy in the meal (Parsons et al., 2000, Poultry Sci. 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that Arabidopsis is an excellent model for oil metabolism in these crops. Biochemical screens of seed oil composition have identified Arabidopsis genes for many critical biosynthetic enzymes and have led to identification of agronomically important gene orthologs. For instance, screens using chemically mutagenized populations have identified lipid mutants whose seeds display altered fatty acid composition (Lemieux et al., 1990, Theor. Appl. Genet. 80: 234-240; James and Dooner, 1990, Theor. Appl. Genet. 80: 241-245). T-DNA mutagenesis screens (Feldmann et al., 1989, Science 243: 1351-1354) that detected altered fatty acid composition identified the omega 3 desaturase (FAD3) and delta-12 desaturase (FAD2) genes (U.S. Pat. No. 5,952,544; Yadav et al., 1993, Plant Physiol. 103: 467-476; Okuley et al., 1994, Plant Cell 6(1):147-158). A screen which focused on oil content rather than oil quality, analyzed chemically-induced mutants for wrinkled seeds or altered seed density, from which altered seed oil content was inferred (Focks and Benning, 1998, Plant Physiol. 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology,* 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9th *International Conference on Arabidopsis Research*, Univ. of Wisconsin-Madison, June 24-28, Abstract 165).

SUMMARY

Provided herein are transgenic plants having a High Oil (HIO) phenotype. Transgenic plants with a High Oil phenotype may include an improved oil quantity and/or an improved meal quality. The HIO phenotype in a transgenic plant may also include altered protein and/or fiber content in any part of the transgenic plant, for example in the seeds or an altered oil content in any part of the transgenic plant, for example in the seeds. In some embodiments of a transgenic plant, the HIO phenotype is an increase in the oil content of the seed (a high oil phenotype). In other embodiments, the HIO phenotype may be an increase in protein content in the seed and/or a decrease in the fiber content of the seed. Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an HIO phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Examples of the disclosed transgenic plant are produced by a method that comprises introducing into progenitor cells of the plant a plant transformation vector comprising a HIO nucleotide sequence that encodes, or is complementary to a sequence that encodes, a HIO polypeptide, and growing the transformed progenitor cells to produce a transgenic plant, wherein the HIO polynucleotide sequence is expressed, causing a HIO phenotype in the transgenic plant. In some specific, non-limiting examples, the method produces transgenic plants wherein expression of the HIO polypeptide causes a high (increased) oil, high (increased) protein, and/or low (decreased) fiber phenotype in the transgenic plant, relative to control, non-transgenic, or wild-type plants.

Additional methods are disclosed herein of generating a plant having a HIO phenotype, wherein a plant is identified that has an allele in its HIO nucleic acid sequence that results in a HIO phenotype, compared to plants lacking the allele. The plant can generate progeny, wherein the progeny inherit the allele and have an HIO phenotype. In some embodiments of the method, the method employs candidate gene/QTL methodology or TILLING methodology.

Also provided herein is a transgenic plant cell having a HIO phenotype. The transgenic plant cell comprises a transformation vector comprising a HIO nucleotide sequence that encodes or is complementary to a sequence that encodes a HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "HIO phenotype" refers to plants, or any part of a plant (for example, seeds, or meal produced from seeds), with an altered oil, protein, and/or fiber content (phenotype). As provided herein, altered oil, protein and/or fiber content includes either an increased or decreased level of oil, protein and/or fiber content in plants, seeds or seed meal. Any combination of these changes can lead to a HIO phenotype. For example, in one specific non-limiting example, a HIO phenotype can refer to increased oil and decreased fiber content. In another specific non-limiting example, a HIO phenotype can refer to unchanged protein and decreased fiber content. In another specific non-limiting example, an HIO phenotype can refer to increased oil and protein and decreased fiber. In yet another specific non-limiting example, a HIO phenotype can refer to increased oil and protein and unchanged fiber content. It is also provided that any combination of these changes can lead to an increase in the AME (available metabolizable energy) from the seed or meal generated from the seed. A HIO phenotype also includes an improved seed quality (ISQ) phenotype or an improved seed meal quality phenotype.

As used herein, the term "HIO phenotype" refers to plants, or any part of a plant (for example, seeds), with an altered oil content (phenotype). As provided herein, altered oil content includes an increased, for example a high, oil content in plants or seeds. In specific, non-limiting examples, a transgenic plant having a combination of an HIO phenotype can lead to an increase in the AME (available metabolizable energy) from the seed or meal generated from the seed. An HIO phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed oil, digestible protein, total protein and/or fiber content, resulting in an increase in the value of animal feed derived from the seed.

As used herein, the term "content" refers to the type and relative amount of, for instance, a seed or seed meal component.

As used herein, the term "seed oil" refers to the total amount of oil within the seed.

As used herein, the term "seed fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "seed total protein" refers to the total amount of protein within the seed.

As used herein, the term "seed digestible protein" refers to the seed protein that is able to be digested by enzymes in the digestive track of an animal. It is a subset of the total protein content.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog or paralog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression"

and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an HIO phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Likewise, a decrease in oil content includes about a 1.0%, 1.5%, 2.0%, 2.5%, 3.0%, 3.5%, 4.0%, 4.5%, 5.0%, 7.5%, 10%, or more decrease in oil content, in various embodiments.

The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified (non-transgenic) plant. A high protein phenotype refers to an increase in overall protein content. An increase in protein content includes, in various embodiments, about a 1.0%, 1.5%, 2.0%, 2.5%, 3.0%, 3.5%, 4.0%, 4.5%, 5.0%, 7.5%, 10%, or more increase in total protein content. Likewise, a decrease in protein content includes about a 1.0%, 1.5%, 2.0%, 2.5%, 3.0%, 3.5%, 4.0%, 4.5%, 5.0%, 7.5%, 10%, or more decrease in total protein content, in various embodiments. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified (non-transgenic) plant. A low fiber phenotype refers to decrease in overall fiber content. An increase in fiber content includes about a 1.0%, 1.5%, 2.0%, 2.5%, 3.0%, 3.5%, 4.0%, 4.5%, 5.0%, 7.5%, 10%, or more increase in fiber content. Likewise, a decrease in fiber content includes about a 1.0%, 1.5%, 2.0%, 2.5%, 3.0%, 3.5%, 4.0%, 4.5%, 5.0%, 7.5%, 10%, or more decrease in fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an HIO phenotype. The transgenic plant cell comprises a transformation vector comprising an HIO nucleotide sequence that encodes or is complementary to a sequence that encodes an HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having High Oil phenotype. Transgenic plants with High Oil phenotype may include an improved oil quantity and/or an improved meal quality, as compared to the similar, but non-modified (non-transgenic) plant. Transgenic plants with improved meal quality have a HIO phenotype and transgenic plants with improved oil quantity have a HIO phenotype. The HIO phenotype in a transgenic plant may also include altered protein and/or fiber content in any part of the transgenic plant, for example in the seeds, as compared to the similar, but non-modified (non-transgenic) plant. The HIO phenotype in a transgenic plant may include altered oil content in any part of the transgenic plant, for example in the seeds, as compared to the similar, but non-modified (non-transgenic) plant. In particular embodiments, a transgenic plant may include a HIO phenotype. In some embodiments of a transgenic plant, the HIO phenotype may be an increase in protein content in the seed and/or a decrease in the fiber content of the seed. An increase in protein content includes about a 1.0%, 1.5%, 2.0%, 2.5%, 3.0%, 3.5%, 4.0%, 4.5%, 5.0%, 7.5%, 10%, or more increase in protein content, for instance total protein content. A decrease in fiber content includes about a 1.0%, 1.5%, 2.0%, 2.5%, 3.0%, 3.5%, 4.0%, 4.5%, 5.0%, 7.5%, 10%, or more decrease in fiber content.

In other embodiments of a transgenic plant, the HIO phenotype includes an increase in the oil content of the seed (a high oil phenotype) from the plant, as compared to the similar, but non-modified (non-transgenic) plant. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. An increase in the AME includes about a 1.0%, 1.5%, 2.0%, 2.5%, 3.0%, 3.5%, 4.0%, 4.5%, 5.0%, 7.5%, 10%, or more increase in AME in the seed or seed meal, in various embodiments. Also provided herein is meal, feed, or food produced from any part of the transgenic plant with an HIO phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill or limit the growth of the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610, 042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin, neomycin, G418, bleomycin, methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered oil, protein and/or fiber content (see columns 4, 5 and 6 respectively, of Table 1, below) and 2) the nucleic acid sequences identified in column 3 of Tables 2 and 3, wherein each nucleic acid sequence is provided with a gene alias or a HIO designation (HIO#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000, *Plant Physiology*, 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

The association of a HIO nucleic acid sequence with a HIO phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed HIO nucleic acid sequences and/or polypeptides may be employed in the development of transgenic plants having a high oil (HIO) phenotype. HIO nucleic acid sequences may be used in the generation of transgenic plants, such as oilseed crops, that provide improved oil yield from oilseed processing and result in an increase in the quantity of oil recovered from seeds of the transgenic plant. HIO nucleic acid sequences may also be used in the generation of transgenic plants, such as feed grain crops, that provide an HIO phenotype resulting in increased energy for animal feeding, for example, seeds or seed meal with an altered protein and/or fiber content, resulting in an increase in AME. HIO nucleic acid sequences may further be used to increase the oil content of specialty oil crops, in order to augment yield and/or recovery of desired unusual fatty acids. Transgenic plants that have been genetically modified to express HIO polypeptides can be used in the production of seeds, wherein the transgenic plants are grown, and oil and seed meal are obtained from plant parts (e.g. seed) using standard methods.

HIO Nucleic Acids and Polypeptides

The HIO designation for each of the HIO nucleic acid sequences discovered in the activation tagging screen described herein are listed in column 1 of Tables 1-3, below. The disclosed HIO polypeptides are listed in column 4 of Tables 2 and 3, below. As used herein, the term "HIO polypeptide" refers to any polypeptide that when expressed in a plant causes an HIO phenotype in any part of the plant, for example the seeds. In one embodiment, a HIO polypeptide refers to a full-length HIO protein, or a fragment, derivative (variant), or ortholog or paralog thereof that is "functionally active," such that the protein fragment, derivative, or ortholog or paralog exhibits one or more or the functional activities associated with one or more of the disclosed full-length HIO polypeptides, for example, the amino acid sequences provided in the GenBank entry referenced in column 5 of Table 2, and column 4 of Table 3 which correspond to the amino acid sequences set forth as SEQ ID NO: 2, SEQ ID NO: 4, SEQ ID NO: 6, or SEQ ID NO: 8, or an ortholog or paralog thereof. In one preferred embodiment, a functionally active HIO polypeptide causes a HIO phenotype in a transgenic plant. In another embodiment, a functionally active HIO polypeptide causes an altered oil, protein, and/or fiber content phenotype (for example, an altered seed meal content phenotype) when mis-expressed in a plant. In other preferred embodiments, mis-expression of the HIO polypeptide causes a high oil (such as, increased oil), high protein (such as, increased protein), and/or low fiber (such as, decreased fiber) phenotype in a plant. In another embodiment, mis-expression of the HIO polypeptide causes an improved AME of meal. In yet another embodiment, a functionally active HIO polypeptide can rescue defective (including deficient) endogenous HIO activity when expressed in a plant or in plant cells; the rescuing polypeptide may be from the same or from a different species as the species with the defective polypeptide activity. The disclosure also provides feed, meal, grain, food, or seed comprising the HIO polypeptide, or a fragment, derivative (variant), or ortholog or paralog thereof.

In another embodiment, a functionally active fragment of a full length HIO polypeptide (for example, a functionally active fragment of a native polypeptide having the amino acid sequence set forth as SEQ ID NO: 2, SEQ ID NO: 4, SEQ ID NO: 6, or SEQ ID NO: 8, or a naturally occurring ortholog or paralog thereof) retains one or more of the biological properties associated with the full-length HIO polypeptide, such as signaling activity, binding activity, catalytic activity, or cellular or extra-cellular localizing activity. A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 7 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length HIO polypeptides, or fragments thereof, include polypeptides with amino acid insertions, deletions, or substitutions that retain one of more of the biological properties associated with the full-length HIO polypeptide. In some cases, variants are generated that change the post-translational processing of an HIO polypeptide. For instance, variants may have altered protein transport or protein localization characteristics, or altered protein half-life, compared to the native polypeptide.

As used herein, the term "HIO nucleic acid" refers to any polynucleotide that when expressed in a plant causes a HIO phenotype in any part of the plant, for example the seeds. In one embodiment, a HIO polynucleotide encompasses nucleic acids with the sequence provided in or complementary to the GenBank entry referenced in column 3 of Tables 2 and 3, which correspond to nucleic acid sequences set forth as SEQ ID NO: 1, SEQ ID NO: 3, SEQ ID NO: 5, or SEQ ID NO: 7, as well as functionally active fragments, derivatives, or orthologs or paralogs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. A functionally active HIO nucleic acid also includes genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes an HIO polypeptide.

In one preferred embodiment, a HIO nucleic acid used in the disclosed methods comprises a nucleic acid sequence that encodes, or is complementary to a sequence that encodes, a HIO polypeptide having at least 50%, 60%, 70%, 75%, 80%, 85%, 90%, 95%, 97%, 98%, or 99% sequence identity to a disclosed HIO polypeptide sequence, for example the amino acid sequence set forth as SEQ ID NO: 2, SEQ ID NO: 4, SEQ ID NO: 6, or SEQ ID NO: 8.

In another embodiment, a HIO polypeptide comprises a polypeptide sequence with at least 50% or 60% identity to a disclosed HIO polypeptide sequence (for example, the amino acid sequence set forth as SEQ ID NO: 2, SEQ ID NO: 4, SEQ ID NO: 6, or SEQ ID NO: 8) and may have at least 70%, 80%, 85%, 90%, 95%, 97%, 98%, or 99% sequence identity to a disclosed HIO polypeptide sequence. In a further embodiment, a HIO polypeptide comprises 50%, 60%, 70%, 80%, 85%, 90%, 95%, 97%, 98%, or 99% sequence identity to a disclosed HIO polypeptide sequence, and may include a conserved protein domain of the HIO polypeptide (such as the protein domain(s) listed in column 7 of Table 2). In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, a HIO polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 7 of Table 2.

In another aspect, a HIO polynucleotide sequence is at least 50% to 60% identical over its entire length to a disclosed HIO nucleic acid sequence, such as the nucleic acid sequence set forth as SEQ ID NO: 1, SEQ ID NO: 3, SEQ ID NO: 5, or SEQ ID NO: 7, or nucleic acid sequences that are complementary to such a HIO sequence, and may comprise at least 70%, 80%, 85%, 90%, 95%, 97%, 98%, or 99% sequence identity to the disclosed HIO sequence, or a functionally active fragment thereof, or complementary sequences. In another embodiment, a disclosed HIO nucleic acid comprises a nucleic acid sequence as shown in SEQ ID NO: 1, SEQ ID NO: 3, SEQ ID NO: 5, or SEQ ID NO: 7, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e., the sequences function in substantially the same manner and encode an HIO polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed HIO nucleic acid sequences (for example, the nucleic acid sequence set forth as SEQ ID NO: 1, SEQ ID NO: 3, SEQ ID NO: 5, or SEQ ID NO: 7). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs (and/or paralogs) of a disclosed *Arabidopsis* HIO nucleic acid sequence. Representative putative orthologs (and/or paralogs) of each of the disclosed *Arabidopsis* HIO genes are identified in column 5 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research*, 10:1204-1210).

Programs for multiple sequence alignment, such as CLUSTAL (Thompson J D et al., 1994, *Nucleic Acids Res.* 22:4673-4680) may be used to highlight conserved regions and/or residues of homologous (orthologous and/or paralogous) proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of SEQ ID NO: 1, SEQ ID NO: 3, SEQ ID NO: 5, or SEQ ID NO: 7 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog (and/or paralog) isolation (see, e.g., Harlow and Lane, 1988, 1999, *Antibodies: A Laboratory Manual*, Cold Spring Harbor Laboratory Press, New York). Western blot analysis can determine that a HIO ortholog (i.e., a protein orthologous to a disclosed HIO polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the HIO nucleic acid into a plant expression vector for transformation of plant cells, and the HIO polypeptide is expressed in the host plant. Transformed plants and plant cells expressing an HIO polypeptide express a HIO phenotype and, in one specific, non-limiting example, may have high (increased) oil, high (increased) protein, and/or low (decreased) fiber content.

An "isolated" HIO nucleic acid molecule is other than in the form or setting in which it is found in nature, and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express HIO where, for example, the nucleic acid molecule is in a chromosomal location different from that of natural cells.

Generation of Genetically Modified Plants with an Improved Oil Quantity Phenotype and/or an Improved Meal Quality Phenotype The disclosed HIO nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the HIO gene in a plant is used to generate plants with a high oil content (phenotype). As used herein, an "altered total protein content (phenotype)" may refer to altered protein content in any part of the plant. In a preferred embodiment, altered expression of the HIO gene in a plant is used to generate plants with a high (or increased) total protein content (phenotype). As used herein, an "altered fiber content (phenotype)" may refer to altered fiber content in any part of the plant. In a preferred embodiment, altered expression of the HIO gene in a plant is used to generate plants with a low (or decreased) fiber content (phenotype). The altered oil, protein and/or fiber content is often observed in seeds. Examples of a transgenic plant include plants comprising a plant transformation vector with a nucleotide sequence that encodes or is complementary to a sequence that encodes an HIO polypeptide having the amino acid sequence as set forth in SEQ ID NO: 2, SEQ ID NO: 4, SEQ ID NO: 6, or SEQ ID NO: 8, or an ortholog or paralog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the HIO nucleic acid sequence (or an ortholog, paralog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the HIO nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), maize (Ishida et al., 1996 *Nature Biotechnol.* 14:745-750, Zhang et al., 2002 *Plant Cell Rep.* 21:263-270) sunflower (Everett et al., 1987, *Bio/Technology*, 5:1201), soybean (Christou et al., 1989, *Proc. Natl. Acad. Sci. USA,* 86:7500-7504; Kline et al., 1987, *Nature,* 327:70), wheat, rice and oat.

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of a HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci. (U.S.A.)* 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci. (U.S.A.)* 84:6624-6628, 1987), the sucrose synthase promoter (Yang et al., *Proc. Natl. Acad. Sci. (U.S.A.)* 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol. Biol.,* 37:1055-1067), and the melon actin promoter (published PCT application WO0056863). Exemplary tissue-specific promoters include the tomato E4 and E8 promoters (U.S. Pat. No. 5,859,330), the tomato 2AII gene promoter (Van Haaren M J J et al., 1993, *Plant Mol Bio.,* 21:625-640) and the PRU promoter that gives seed-associated gene expression (U.S. Pat. No. 7,179,960).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209: 219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 *oleosin* promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7Sα' promoter (U.S. Application No. 2003/0093828), the soybean 7Sα' beta conglycinin promoter, a 7Sα' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf. Usp, SEQ ID NO: 1, 2, and 3 in (U.S. Application No. 2003/229918) and *Zea mays* L3 *oleosin* promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2): 157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In another embodiment, the endogenous HIO gene may be placed under the control of a transgenic transcription factor or used to design binding sites that modulates its expression. One such class of transcription factors are the $Cys_2$-$His_2$-zinc finger proteins (ZFPs). ZFPs are common DNA binding proteins and can be designed to specifically bind to specific DNA sequences (Beerli & Barbas, Nat Biotechnol., 2002, 20:135-141., Gommans et al., J Mol Biol., 2005, 354:507-519). Individual zinc-finger domains are composed of approximately 30 amino acids, are structurally conserved and can interact with 3-4 bp of DNA. A polypeptide containing multiple zinc-fingers designed to bind to a specific DNA sequence in the promoter of a HIO gene can be synthesized. The principles for designing the zinc finger domains to interact with specific DNA sequences have been described in Segal et al., (Segal et al., Proc Natl Acad Sci USA., 1999, 96:2758-2763), Dreier et al. (Dreier et al., J Mol Biol., 2000, 303:489-502), and Beerli and Barbas (Beerli & Barbas, Nat Biotechnol., 2002, 20:135-141). These DNA binding domains may be fused to effector domains to form a synthetic ZFP that may regulate transcription of genes to which they bind. Effector domains that can activate transcription include but are not limited to the acidic portion of the herpes simplex virus protein VP16 (Sadowski et al., Nature., 1988, 335:563-564) and VP64 (Beerli et al., Proc Natl Acad Sci USA., 1998, 95:14628-14633), and the NF-κB transcription factor p65 domain (Bae et al., Nat Biotechnol., 2003, 21:275-280., Liu et al., J Biol Chem., 2001, 276:11323-11334). Effector domains that can repress transcription include but are not limited to mSIN3 and KRAB (Ayer et al., Mol Cell Biol., 1996, 16:5772-5781, Beerli & Barbas, Nat Biotechnol., 2002, 20:135-141, Beerli et al., Proc Natl Acad Sci USA, 1998, 95:14628-14633, Margolin et al., Proc Natl Acad Sci USA., 1994, 91:4509-4513). These approaches have been shown to work in plants (Guan et al., Proc Natl Acad Sci U S A., 2002, 99:13296-13301, Stege et al., Plant J., 2002, 32:1077-1086, Van Eenennaam et al., Metab Eng., 2004, 6:101-108).

In yet another aspect, in some cases it may be desirable to inhibit the expression of the endogenous HIO nucleic acid sequence in a host cell. Exemplary methods for practicing this aspect of the invention include, but are not limited to antisense suppression (Smith, et al., 1988, *Nature*, 334:724-726; van der Krol et al., 1988, *BioTechniques*, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Natl. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.
Generation of Mutated Plants with a High Oil Phenotype and/or Improved Meal Quality Phenotype Additional methods are disclosed herein of generating a plant having a HIO phenotype, wherein a plant is identified that has an allele in its HIO nucleic acid sequence that results in an HIO phenotype, compared to plants lacking the allele. The plant can generate progeny, wherein the progeny inherit the allele and have a HIO phenotype. For example, provided herein is a method of identifying plants that have mutations in the endogenous HIO nucleic acid sequence that confer an HIO phenotype and generating progeny of these plants with an HIO that are not genetically modified. In some embodiments, the plants have a HIO phenotype with an altered oil, protein and/or fiber content or seed meal content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the HIO nucleic acid sequence is used to identify whether a mutated plant has a mutation in the HIO nucleic acid sequence. Plants having HIO mutations may then be tested for altered oil, protein, and/or fiber content, or alternatively, plants may be tested for altered oil, protein, and/or fiber content, and then PCR amplification and sequencing of the HIO nucleic acid sequence is used to determine whether a plant having altered oil, protein, and/or fiber content has a mutated HIO nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the HIO nucleic acid sequence or orthologs (and/or paralogs) of the HIO nucleic acid sequence that may confer altered oil, protein, and/or fiber content (see Bert et al., *Theor Appl Genet.*, 2003 June; 107(1):181-9; and Lionneton et al., *Genome*, 2002 December; 45(6):1203-15). Thus, in a further aspect of the disclosure, a HIO nucleic acid is used to identify whether a plant having altered oil, protein, and/or fiber content has a mutation an endogenous HIO nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents and patent applications are incorporated by reference. Sequence information in referenced public databases is also incorporated by reference as of Jun. 18, 2007, unless indicated otherwise.

EXAMPLES

Example 1

Generation of Plants with a HIO Phenotype by Transformation with an Activation Tagging Construct This Example describes the generation of transgenic plants with altered oil, protein, and/or fiber content.

Mutants were generated using the activation tagging "ACT-TAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

Quantitative determination of fatty acid content in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 μl 2.5% $H_2SO_4$ in MeOH for 3 hours at 80° C., following the method of Browse et al. (Biochem J 235: 25-31, 1986) with modifications. A known amount of heptadecanoic acid was included in the reaction as an internal standard. 750 μl of water and 400 μl of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 μm film thickness). The carrier gas was Hydrogen at a constant flow of 2.5 ml/minute. 1 μl of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR total protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A NIR fiber content predicting calibration was developed using crude fiber content data of seed samples following the general method of AOAC Official Method 962.09 (Official Methods of Analysis of AOAC International 17$^{th}$ Edition AOAC, Gaithersburg, Md.).

Oil, protein and fiber predictions from NIR spectra were compared for 82,274 individual ACTTAG lines. Subsequent to seed compositional analysis, the position of the ACTTAG element in the genome in each line was determined by inverse PCR and sequencing. 37,995 lines with recovered flanking sequences were considered in this analysis.

Seed oil, and protein values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Generally, promoters within 9 kb of the enhancers in the ACTTAG element are considered to be within "activation space." Genes with T-DNA inserts within coding sequences were not considered to be within "activation space." The ACTTAG lines identified are listed in column 3 of Table 1. In some cases more than one ACTTAG line is associated with a gene.

TABLE 1

| 1. Gene alias | 2. Tair | 3. ACTTAG Line Number | 4. Relative Oil | 5. Method |
|---|---|---|---|---|
| HIO110-G | At1g47780 | IN022173 | 107% | NIR |
| HIO110-G | At1g47780 | IN023577 | 107% | NIR |
| HIO32-B | At3g47700 | W000082263 | 107-112% | GC |

Example 2

Analysis of the *Arabidopsis* HIO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318). Conserved domains in each gene are listed in Table 2. The GenBank number for the closest ortholog of each gene is listed in Table 3.

TABLE 2

| 1. Gene alias | 2. Tair | 3. Genomic sequence in BAC clone** | 4. cDNA sequence. GI# | 5. Polypeptide seq. GI# | 6. Putative biochemical function/protein name | 7. Conserved protein domains |
|---|---|---|---|---|---|---|
| HIO110-G | At1g47780 | Complement of residues 48056-48716 of gi\|9743359 | gi\|18401894 SEQ ID NO: 1 | gi\|15220956 SEQ ID NO: 2 | acyl-protein thioesterase-related [*Arabidopsis thaliana*] | None |
| HIO110-G | At1g47780 | Complement of residues 48056-48716 of gi\|9743359 | gi\|18401904 SEQ ID NO: 3 | gi\|15220962 SEQ ID NO: 4 | acyl-protein thioesterase-related [*Arabidopsis thaliana*] | PF02230 Abhydrolase_2 |
| HIO32-B | At3g47700 | Complement of residues 7938-10743 of gi\|4741184 | gi\|22331643 SEQ ID NO: 5 | gi\|15228233 SEQ ID NO: 6 | MAG2 [*Arabidopsis thaliana*] | PF04437 RINT1_TIP1 RINT-1/TIP-1 family |
| HIO32-B | At3g47700 | Complement of residues 7938-10743 of gi\|4741184 | gi\|30680622 SEQ ID NO: 7 | gi\|30680623 SEQ ID NO: 8 | chromosome structural maintenance protein-related [*Arabidopsis thalian* | PF04437 RINT1_TIP1 RINT-1/TIP-1 family |

**Incorporated by reference as of Jun. 17, 2008

TABLE 3

| 1. Gene alias | 2. Tair | 3. Nucleir Acid seq. GI# | 4. Polypeptide seq. GI# | 5. Putative biochemical function/protein name | 6. Nucleic Acid GI# | 7. Polypeptide GI# | 8. Species |
|---|---|---|---|---|---|---|---|
| HIO110-G | At1g47780 | gi\|18401894 SEQ ID NO: 1 | gi\|15220956 SEQ ID NO: 2 | acyl-protein thioesterase-related [Arabidopsis thaliana] | gi\|18401904 | gi\|15220962 | Arabidopsis thaliana |
| | | | | | gi\|91805936 | gi\|91805937 | None |
| | | | | | gi\|42570232 | gi\|30695308 | Arabidopsis thaliana |
| | | | | | gi\|145338555 | gi\|15232645 | Arabidopsis thaliana |
| | | | | | gi\|42562706 | gi\|42562707 | Arabidopsis thaliana |
| HIO110-G | At1g47780 | gi\|18401904 SEQ ID NO: 3 | gi\|15220962 SEQ ID NO: 4 | acyl-protein thioesterase-related [Arabidopsis thaliana] | gi\|18401894 | gi\|15220956 | Arabidopsis thaliana |
| | | | | | gi\|42570232 | gi\|30695308 | Arabidopsis thaliana |
| | | | | | gi\|145338555 | gi\|15232645 | Arabidopsis thaliana |
| | | | | | gi\|91805936 | gi\|91805937 | None |
| | | | | | gi\|42562706 | gi\|42562707 | Arabidopsis thaliana |
| HIO32-B | At3g47700 | gi\|22331643 SEQ ID NO: 5 | gi\|15228233 SEQ ID NO: 6 | MAG2 [Arabidopsis thaliana] | gi\|115448678 | gi\|115448679 | Oryza sativa (japonica cultivar-group) |
| | | | | | gi\|30680622 | gi\|30680623 | Arabidopsis thaliana |
| | | | | | gi\|115474174 | gi\|115474175 | Oryza sativa (japonica cultivar-group) |
| | | | | | gi\|26324645 | gi\|26324646 | Mus musculus |
| | | | | | gi\|118082073 | gi\|118082074 | None |
| HIO32-B | At3g47700 | gi\|30680622 SEQ ID NO: 7 | gi\|30680623 SEQ ID NO: 8 | chromosome structural maintenance protein-related [Arabidopsis thalian | gi\|115474174 | gi\|115474175 | Oryza sativa (japonica cultivar-group) |
| | | | | | gi\|22331643 | gi\|15228233 | Arabidopsis thaliana |
| | | | | | gi\|115448678 | gi\|115448679 | Oryza sativa (japonica cultivar-group) |
| | | | | | gi\|33346978 | gi\|116509765 | None |
| | | | | | gi\|116003878 | gi\|116003879 | None |

Example 3

Generation of Transgenic Plants

To test whether over-expression of the genes in Table 2 alter the seed composition phenotype, protein, digestible protein, oil and fiber content in seeds from transgenic plants expressing this gene was compared with oil content in seeds from non-transgenic control plants. To do this, genomic copies of these genes (column 3, Table 2) were cloned into a plant transformation vector behind the strong constitutive CsVMV promoter or the seed specific PRU promoter (see Examples 4-7, below). These constructs were transformed into Arabidopsis plants using the floral dip method. The plant transformation vector contains the nptII gene, which provides resistance to kanamycin, and serves as a selectable marker. Seed from the transformed plants were plated on agar medium containing kanamycin. After 10 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and their oil, protein and fiber content estimated by Near Infrared (NIR) Spectroscopy using methods previously described.

Example 4

Recapitulation of HIO110-G (At1g47780)

The effect of seed specific-expression of At1g47780 on seed oil, protein and fiber has been tested in three experiments. The relative measures of each seed component were determined by dividing the value for each component by the average of the control values. Plants expressing the CsVMV::At1g47780 transgene had significantly more oil (103.6%) but no significant difference in seed protein and fiber than control plants (ANOVA p values>0.05). The data for the experiments are shown in Table 4.

TABLE 4

| Experiment | Plant | Transgene | Relative Protein | Relative Oil | Relative Fiber |
|---|---|---|---|---|---|
| 1 | Z003926001 | CSVMV::HIO110-1 G | 100.40 | 98.10 | 98.15 |
| 1 | Z003926002 | CSVMV::HIO110-1 G | 93.87 | 106.01 | 103.13 |
| 1 | Z003926003 | CSVMV::HIO110-1 G | 89.97 | 107.13 | 101.12 |
| 1 | Z003926004 | CSVMV::HIO110-1 G | 90.19 | 106.99 | 102.03 |
| 1 | Z003926005 | CSVMV::HIO110-1 G | 89.19 | 108.23 | 98.88 |
| 1 | Z003926006 | CSVMV::HIO110-1 G | 97.21 | 101.52 | 99.12 |
| 1 | Z003926007 | CSVMV::HIO110-1 G | 99.96 | 97.11 | 100.39 |
| 1 | Z003926008 | CSVMV::HIO110-1 G | 101.00 | 99.84 | 97.04 |
| 1 | Z003926009 | CSVMV::HIO110-1 G | 91.46 | 108.95 | 103.59 |
| 1 | Z003926010 | CSVMV::HIO110-1 G | 111.08 | 95.60 | 95.05 |
| 1 | Z003926011 | CSVMV::HIO110-1 G | 105.09 | 100.59 | 94.41 |
| 1 | Z003926013 | CSVMV::HIO110-1 G | 86.71 | 108.90 | 103.60 |
| 1 | Z003926014 | CSVMV::HIO110-1 G | 88.72 | 112.28 | 106.43 |
| 1 | Z003926015 | CSVMV::HIO110-1 G | 93.34 | 109.27 | 106.27 |
| 1 | Z003926016 | CSVMV::HIO110-1 G | 100.18 | 100.55 | 96.34 |
| 1 | Z003926017 | CSVMV::HIO110-1 G | 97.03 | 103.03 | 103.55 |
| 1 | Z003926018 | CSVMV::HIO110-1 G | 99.53 | 102.64 | 97.03 |
| 1 | Z003926019 | CSVMV::HIO110-1 G | 97.75 | 103.15 | 104.89 |
| 1 | Z003926020 | CSVMV::HIO110-1 G | 111.61 | 89.76 | 98.40 |
| 1 | Z003926021 | CSVMV::HIO110-1 G | 98.27 | 106.39 | 105.59 |
| 1 | Z003926022 | CSVMV::HIO110-1 G | 98.24 | 100.39 | 102.54 |
| 1 | Z003912001 | COL-0 | 115.64 | 85.97 | 92.11 |
| 1 | Z003912002 | COL-0 | 99.86 | 102.98 | 98.74 |
| 1 | Z003912003 | COL-0 | 96.70 | 100.73 | 102.75 |
| 1 | Z003912004 | COL-0 | 93.99 | 103.84 | 102.64 |
| 1 | Z003912005 | COL-0 | 100.80 | 98.55 | 95.36 |
| 1 | Z003912006 | COL-0 | 91.91 | 102.69 | 104.12 |
| 1 | Z003912008 | COL-0 | 100.07 | 101.66 | 98.49 |
| 1 | Z003912009 | COL-0 | 94.90 | 105.35 | 104.28 |
| 1 | Z003912010 | COL-0 | 106.12 | 98.24 | 101.50 |
| 2 | Z003987001 | CSVMV::HIO110-1 G | 97.36 | 107.91 | 100.35 |
| 2 | Z003987002 | CSVMV::HIO110-1 G | 101.44 | 101.76 | 97.07 |
| 2 | Z003987003 | CSVMV::HIO110-1 G | 96.71 | 103.60 | 97.73 |
| 2 | Z003987004 | CSVMV::HIO110-1 G | 102.90 | 96.62 | 99.39 |
| 2 | Z003987005 | CSVMV::HIO110-1 G | 97.35 | 101.79 | 100.24 |
| 2 | Z003987006 | CSVMV::HIO110-1 G | 94.34 | 101.36 | 100.61 |
| 2 | Z003987007 | CSVMV::HIO110-1 G | 100.44 | 96.66 | 100.76 |
| 2 | Z003987008 | CSVMV::HIO110-1 G | 96.43 | 100.70 | 97.63 |
| 2 | Z003987009 | CSVMV::HIO110-1 G | 101.95 | 97.82 | 91.44 |
| 2 | Z003987010 | CSVMV::HIO110-1 G | 102.71 | 102.54 | 94.46 |
| 2 | Z003987011 | CSVMV::HIO110-1 G | 103.65 | 99.91 | 93.16 |
| 2 | Z003987012 | CSVMV::HIO110-1 G | 94.45 | 103.29 | 102.29 |
| 2 | Z003987013 | CSVMV::HIO110-1 G | 93.43 | 107.74 | 103.91 |
| 2 | Z003987014 | CSVMV::HIO110-1 G | 88.04 | 114.22 | 103.27 |
| 2 | Z003987015 | CSVMV::HIO110-1 G | 96.00 | 106.83 | 102.59 |
| 2 | Z003987016 | CSVMV::HIO110-1 G | 99.70 | 101.83 | 100.89 |
| 2 | Z003987017 | CSVMV::HIO110-1 G | 91.94 | 111.49 | 107.60 |
| 2 | Z003987018 | CSVMV::HIO110-1 G | 97.65 | 106.85 | 103.36 |
| 2 | Z003987019 | CSVMV::HIO110-1 G | 90.20 | 111.13 | 105.10 |
| 2 | Z003987020 | CSVMV::HIO110-1 G | 94.23 | 108.00 | 103.49 |
| 2 | Z003987021 | CSVMV::HIO110-1 G | 99.73 | 105.17 | 98.60 |
| 2 | Z003987022 | CSVMV::HIO110-1 G | 96.83 | 103.27 | 106.86 |
| 2 | Z004003001 | COL-0 | 91.88 | 107.95 | 104.76 |
| 2 | Z004003002 | COL-0 | 102.76 | 99.29 | 100.24 |
| 2 | Z004003003 | COL-0 | 103.75 | 90.73 | 98.32 |
| 2 | Z004003004 | COL-0 | 100.64 | 102.63 | 98.24 |
| 2 | Z004003005 | COL-0 | 100.67 | 94.95 | 96.22 |
| 2 | Z004003006 | COL-0 | 98.31 | 102.49 | 102.71 |
| 2 | Z004003007 | COL-0 | 101.80 | 100.48 | 101.70 |
| 2 | Z004003008 | COL-0 | 106.21 | 90.68 | 93.01 |
| 2 | Z004003009 | COL-0 | 99.80 | 106.07 | 100.80 |
| 2 | Z004003010 | COL-0 | 94.18 | 104.73 | 104.01 |

Example 5

Recapitulation of HIO110-G (At1G47780) in T3 Seed

To determine whether the high oil phenotype of transgenic plants containing the CsVMV::HIO110-G construct is heritable over generations, T2 seed from several plants exhibiting the increased oil phenotype were sown on agar plates containing the selective agent. Seedlings able to grow on this medium contain the transgene and were transplanted to soil after 10 days. Seeds from COL-0 control plants were germinated on agar medium lacking the selective agent and were transplanted to soil after 10 days. Transgenic and control plants were grown in random positions in the same tray. The plants were grown to maturity and T3 seed was harvested. The relative measures of each seed component were determined by dividing the value for each component by the average of the control values. T3 plants from two independent transformation events (i.e T1 lines) expressing the CsVMV::At1G47780 transgene were grown in separate experiments. Seed from the transgenic lines had significantly more oil (t-test p values>0.05). The data for the experiments are shown in Table 5.

TABLE 5

| Experiment | T1 Line | Plant | Transgene | Relative Protein | Relative Oil | Relative Fiber |
|---|---|---|---|---|---|---|
| 1 | Z003926015 | DX07403001 | CsVMV::HIO110-G | 92.33 | 113.58 | 106.19 |
| 1 | Z003926015 | DX07403002 | CsVMV::HIO110-G | 104.20 | 101.85 | 100.95 |
| 1 | Z003926015 | DX07403003 | CsVMV::HIO110-G | 96.25 | 109.54 | 104.32 |
| 1 | Z003926015 | DX07403004 | CsVMV::HIO110-G | 95.84 | 109.11 | 104.28 |
| 1 | Z003926015 | DX07403005 | CsVMV::HIO110-G | 96.34 | 103.78 | 102.18 |
| 1 | Z003926015 | DX07403006 | CsVMV::HIO110-G | 96.82 | 107.79 | 104.38 |
| 1 | Z003926015 | DX07403007 | CsVMV::HIO110-G | 100.27 | 104.69 | 102.09 |
| 1 | Z003926015 | DX07403008 | CsVMV::HIO110-G | 98.17 | 109.20 | 103.17 |
| 1 | Z003926015 | DX07403009 | CsVMV::HIO110-G | 98.82 | 103.63 | 100.65 |
| 1 | Z003926015 | DX07403010 | CsVMV::HIO110-G | 98.24 | 105.86 | 104.17 |
| 1 | Z003926015 | DX07403011 | CsVMV::HIO110-G | 94.30 | 111.05 | 110.46 |
| 1 | Z003926015 | DX07403012 | CsVMV::HIO110-G | 91.78 | 113.34 | 105.98 |
| 1 | Z003926015 | DX07403013 | CsVMV::HIO110-G | 99.08 | 107.90 | 103.18 |
| 1 | Z003926015 | DX07403014 | CsVMV::HIO110-G | 94.13 | 109.74 | 109.14 |
| 1 | Z003926015 | DX07403015 | CsVMV::HIO110-G | 94.90 | 106.59 | 102.32 |
| 1 | Z003926015 | DX07403016 | CsVMV::HIO110-G | 92.14 | 110.24 | 106.01 |
| 1 | Z003926015 | DX07403017 | CsVMV::HIO110-G | 91.81 | 111.96 | 103.61 |
| 1 | Z003926015 | DX07403018 | CsVMV::HIO110-G | 104.38 | 97.88 | 94.97 |
| 1 | Z003926015 | DX07403019 | CsVMV::HIO110-G | 94.23 | 110.38 | 105.07 |
| 1 | Z003926015 | DX07403020 | CsVMV::HIO110-G | 99.19 | 99.12 | 105.13 |
| 1 | Z003926015 | DX07403021 | CsVMV::HIO110-G | 94.65 | 107.98 | 106.21 |
| 1 | Z003926015 | DX07403022 | CsVMV::HIO110-G | 100.42 | 102.96 | 95.55 |
| 1 | COL-0 | DX07419001 | COL-0 | 95.97 | 98.22 | 101.83 |
| 1 | COL-0 | DX07419002 | COL-0 | 95.12 | 103.69 | 103.28 |
| 1 | COL-0 | DX07419003 | COL-0 | 105.57 | 96.80 | 98.74 |
| 1 | COL-0 | DX07419004 | COL-0 | 92.34 | 107.07 | 107.53 |
| 1 | COL-0 | DX07419005 | COL-0 | 98.34 | 103.46 | 99.59 |
| 1 | COL-0 | DX07419006 | COL-0 | 106.37 | 93.73 | 96.92 |
| 1 | COL-0 | DX07419007 | COL-0 | 99.70 | 101.76 | 97.08 |
| 1 | COL-0 | DX07419008 | COL-0 | 97.35 | 103.07 | 102.55 |
| 1 | COL-0 | DX07419009 | COL-0 | 103.48 | 96.27 | 96.29 |
| 1 | COL-0 | DX07419010 | COL-0 | 105.77 | 95.93 | 96.19 |
| 2 | Z003926021 | DX07409001 | CsVMV::HIO110-G | 102.23 | 96.68 | 100.62 |
| 2 | Z003926021 | DX07409002 | CsVMV::HIO110-G | 108.99 | 95.79 | 88.14 |
| 2 | Z003926021 | DX07409003 | CsVMV::HIO110-G | 91.18 | 115.45 | 106.63 |
| 2 | Z003926021 | DX07409004 | CsVMV::HIO110-G | 88.59 | 120.07 | 114.14 |
| 2 | Z003926021 | DX07409005 | CsVMV::HIO110-G | 87.28 | 127.25 | 108.80 |
| 2 | Z003926021 | DX07409006 | CsVMV::HIO110-G | 96.69 | 111.84 | 106.01 |
| 2 | Z003926021 | DX07409007 | CsVMV::HIO110-G | 93.14 | 110.89 | 104.03 |
| 2 | Z003926021 | DX07409008 | CsVMV::HIO110-G | 101.58 | 96.30 | 101.36 |
| 2 | Z003926021 | DX07409009 | CsVMV::HIO110-G | 85.16 | 125.95 | 116.61 |
| 2 | Z003926021 | DX07409010 | CsVMV::HIO110-G | 91.93 | 105.19 | 108.93 |
| 2 | Z003926021 | DX07409011 | CsVMV::HIO110-G | 93.57 | 104.41 | 100.35 |
| 2 | Z003926021 | DX07409012 | CsVMV::HIO110-G | 103.42 | 95.23 | 102.84 |
| 2 | Z003926021 | DX07409013 | CsVMV::HIO110-G | 93.02 | 108.72 | 104.95 |
| 2 | Z003926021 | DX07409014 | CsVMV::HIO110-G | 107.50 | 98.50 | 97.79 |
| 2 | Z003926021 | DX07409015 | CsVMV::HIO110-G | 87.70 | 119.25 | 114.98 |
| 2 | Z003926021 | DX07409016 | CsVMV::HIO110-G | 92.51 | 113.20 | 107.64 |
| 2 | Z003926021 | DX07409017 | CsVMV::HIO110-G | 99.43 | 101.45 | 99.86 |
| 2 | Z003926021 | DX07409018 | CsVMV::HIO110-G | 95.20 | 103.34 | 106.78 |
| 2 | Z003926021 | DX07409019 | CsVMV::HIO110-G | 96.90 | 106.09 | 105.12 |
| 2 | Z003926021 | DX07409021 | CsVMV::HIO110-G | 93.95 | 112.42 | 107.39 |
| 2 | Z003926021 | DX07409022 | CsVMV::HIO110-G | 103.56 | 100.30 | 103.18 |
| 2 | COL-0 | DX07425001 | COL-0 | 101.17 | 100.63 | 96.74 |
| 2 | COL-0 | DX07425002 | COL-0 | 104.62 | 97.75 | 95.73 |
| 2 | COL-0 | DX07425003 | COL-0 | 103.63 | 93.19 | 93.39 |
| 2 | COL-0 | DX07425004 | COL-0 | 98.53 | 101.31 | 101.77 |
| 2 | COL-0 | DX07425005 | COL-0 | 93.43 | 108.08 | 107.28 |
| 2 | COL-0 | DX07425006 | COL-0 | 99.17 | 98.32 | 98.00 |
| 2 | COL-0 | DX07425007 | COL-0 | 101.93 | 99.76 | 94.49 |
| 2 | COL-0 | DX07425008 | COL-0 | 95.20 | 100.96 | 104.81 |

TABLE 5-continued

| Experiment | T1 Line | Plant | Transgene | Relative Protein | Relative Oil | Relative Fiber |
|---|---|---|---|---|---|---|
| 2 | COL-0 | DX07425009 | COL-0 | 100.21 | 98.69 | 101.28 |
| 2 | COL-0 | DX07425010 | COL-0 | 102.10 | 101.30 | 106.50 |

Example 6

Recapitulation of HIO32-B (At3g47700)

The effect of seed specific-expression of At3g47700 on seed oil, protein and fiber has been tested in three experiments. The relative measures of each seed component were determined by dividing the value for each component by the average of the control values. Plants expressing the Pru::At3g47700 transgene had significantly more oil (104.9%) and less fiber (92.0%) but no significant difference in seed protein than control plants (ANOVA p values>0.05). The data for the experiments are shown in Table 6.

TABLE 6

| Experiment | Plant | Transgene | Relative Protein | Relative Oil | Relative Fiber |
|---|---|---|---|---|---|
| 1 | G002737001 | Pru::HIO32 B | 100.47 | 104.32 | 103.30 |
| 1 | G002737002 | Pru::HIO32 B | 96.17 | 102.36 | 100.39 |
| 1 | G002737003 | Pru::HIO32 B | 98.59 | 101.93 | 102.86 |
| 1 | G002737004 | Pru::HIO32 B | 106.54 | 99.43 | 103.39 |
| 1 | G002737006 | Pru::HIO32 B | 91.49 | 107.47 | 101.03 |
| 1 | G002737007 | Pru::HIO32 B | 102.01 | 105.51 | 100.94 |
| 1 | G002737008 | Pru::HIO32 B | 104.60 | 96.15 | 97.65 |
| 1 | G002737009 | Pru::HIO32 B | 104.42 | 95.03 | 97.86 |
| 1 | G002737011 | Pru::HIO32 B | 98.76 | 99.54 | 99.97 |
| 1 | G002737012 | Pru::HIO32 B | 99.27 | 99.38 | 101.69 |
| 1 | G002737013 | Pru::HIO32 B | 102.68 | 95.75 | 98.97 |
| 1 | G002737014 | Pru::HIO32 B | 99.67 | 102.98 | 99.60 |
| 1 | G002737015 | Pru::HIO32 B | 103.12 | 95.34 | 98.91 |
| 1 | G002737016 | Pru::HIO32 B | 102.32 | 96.37 | 100.59 |
| 1 | G002737017 | Pru::HIO32 B | 106.15 | 97.27 | 97.41 |
| 1 | G002737018 | Pru::HIO32 B | 103.51 | 96.84 | 95.76 |
| 1 | G002737019 | Pru::HIO32 B | 101.04 | 95.87 | 99.72 |
| 1 | G002737022 | Pru::HIO32 B | 99.70 | 103.90 | 95.34 |
| 1 | G002738001 | None | 89.04 | 109.26 | 106.03 |
| 1 | G002738002 | None | 95.43 | 101.48 | 104.65 |
| 1 | G002738003 | None | 100.96 | 99.36 | 99.49 |
| 1 | G002738004 | None | 103.14 | 98.24 | 94.70 |
| 1 | G002738005 | None | 100.49 | 99.74 | 103.15 |
| 1 | G002738007 | None | 102.76 | 98.49 | 99.26 |
| 1 | G002738008 | None | 100.89 | 99.50 | 99.10 |
| 1 | G002738009 | None | 100.26 | 99.78 | 100.11 |
| 1 | G002738010 | None | 107.03 | 94.14 | 93.50 |
| 2 | DX06811001 | Pru::HIO32 B | 97.96 | 110.40 | 83.67 |
| 2 | DX06811002 | Pru::HIO32 B | 106.39 | 104.35 | 84.69 |
| 2 | DX06811004 | Pru::HIO32 B | 108.32 | 103.97 | 82.36 |
| 2 | DX06811005 | Pru::HIO32 B | 103.19 | 108.78 | 79.57 |
| 2 | DX06811006 | Pru::HIO32 B | 101.32 | 107.98 | 81.06 |
| 2 | DX06811007 | Pru::HIO32 B | 98.25 | 114.31 | 87.75 |
| 2 | DX06811008 | Pru::HIO32 B | 97.87 | 109.72 | 87.03 |
| 2 | DX06811009 | Pru::HIO32 B | 95.88 | 121.20 | 81.02 |
| 2 | DX06811010 | Pru::HIO32 B | 101.70 | 107.91 | 81.62 |
| 2 | DX06811012 | Pru::HIO32 B | 96.66 | 107.48 | 86.85 |
| 2 | DX06811013 | Pru::HIO32 B | 106.59 | 95.85 | 87.38 |
| 2 | DX06811014 | Pru::HIO32 B | 91.92 | 114.67 | 85.74 |
| 2 | DX06811015 | Pru::HIO32 B | 89.34 | 122.73 | 86.04 |
| 2 | DX06811016 | Pru::HIO32 B | 91.93 | 121.78 | 86.51 |
| 2 | DX06811017 | Pru::HIO32 B | 97.35 | 104.95 | 82.23 |
| 2 | DX06811018 | Pru::HIO32 B | 107.76 | 100.79 | 86.65 |
| 2 | DX06811019 | Pru::HIO32 B | 97.12 | 112.76 | 84.19 |
| 2 | DX06811020 | Pru::HIO32 B | 97.21 | 114.48 | 87.31 |
| 2 | DX06811021 | Pru::HIO32 B | 105.14 | 102.87 | 86.53 |
| 2 | DX06793001 | None | 91.71 | 115.88 | 90.22 |
| 2 | DX06793002 | None | 97.57 | 106.15 | 82.80 |
| 2 | DX06793003 | None | 98.19 | 106.45 | 87.93 |
| 2 | DX06793004 | None | 96.48 | 103.63 | 104.16 |
| 2 | DX06793005 | None | 101.72 | 94.44 | 101.67 |
| 2 | DX06793006 | None | 105.80 | 89.63 | 105.64 |
| 2 | DX06793007 | None | 96.31 | 101.78 | 111.79 |
| 2 | DX06793008 | None | 99.35 | 97.84 | 105.93 |
| 2 | DX06793009 | None | 106.42 | 92.95 | 101.89 |
| 2 | DX06793010 | None | 106.45 | 91.24 | 107.96 |

Example 7

Recapitulation of HIO32-B (At3g47700) in T3 Seed

To determine whether the high oil phenotype of transgenic plants containing the PRU::HIO32-B construct is heritable over generations, T2 seed from several plants exhibiting the increased oil phenotype were sown on agar plates containing the selective agent. Seedlings able to grow on this medium contain the transgene and were transplanted to soil after 10 days. Seeds from COL-0 control plants were germinated on agar medium lacking the selective agent and were transplanted to soil after 10 days. Transgenic and control plants were grown in random positions in the same tray. The plants were grown to maturity and T3 seed was harvested. The relative measures of each seed component were determined by dividing the value for each component by the average of the control values. T3 plants from four independent transformation events (i.e T1 lines) expressing the PRU::At3g47700 transgene were grown in separate experiments. Seed from the transgenic lines had significantly more oil but no significant difference in seed protein and fiber than control plants (t-test p values>0.05). The data for the experiments are shown in Table 7.

TABLE 7

| Experiment | Plant | Parent | Transgene | Relative Protein | Relative Oil | Relative Fiber |
|---|---|---|---|---|---|---|
| 1 | DX08605001 | DX06811019 | Pru::HIO32 B | 97.20 | 107.46 | 101.46 |
| 1 | DX08605002 | DX06811019 | Pru::HIO32 B | 101.29 | 102.72 | 102.57 |
| 1 | DX08605003 | DX06811019 | Pru::HIO32 B | 90.25 | 116.03 | 111.52 |
| 1 | DX08605004 | DX06811019 | Pru::HIO32 B | 94.12 | 109.62 | 103.38 |
| 1 | DX08605005 | DX06811019 | Pru::HIO32 B | 104.06 | 105.27 | 98.54 |
| 1 | DX08605006 | DX06811019 | Pru::HIO32 B | 113.28 | 98.07 | 93.63 |
| 1 | DX08605007 | DX06811019 | Pru::HIO32 B | 106.44 | 94.08 | 94.83 |

TABLE 7-continued

| Experiment | Plant | Parent | Transgene | Relative Protein | Relative Oil | Relative Fiber |
|---|---|---|---|---|---|---|
| 1 | DX08605008 | DX06811019 | Pru::HIO32 B | 105.39 | 96.60 | 97.81 |
| 1 | DX08605009 | DX06811019 | Pru::HIO32 B | 102.44 | 103.26 | 100.40 |
| 1 | DX08605010 | DX06811019 | Pru::HIO32 B | 96.22 | 113.44 | 108.72 |
| 1 | DX08605011 | DX06811019 | Pru::HIO32 B | 89.48 | 114.50 | 105.15 |
| 1 | DX08605012 | DX06811019 | Pru::HIO32 B | 105.15 | 104.83 | 100.35 |
| 1 | DX08605013 | DX06811019 | Pru::HIO32 B | 94.28 | 107.98 | 102.28 |
| 1 | DX08605014 | DX06811019 | Pru::HIO32 B | 94.90 | 106.50 | 107.69 |
| 1 | DX08605015 | DX06811019 | Pru::HIO32 B | 92.36 | 110.78 | 107.54 |
| 1 | DX08605016 | DX06811019 | Pru::HIO32 B | 90.76 | 111.74 | 105.64 |
| 1 | DX08605017 | DX06811019 | Pru::HIO32 B | 84.74 | 116.02 | 110.63 |
| 1 | DX08605018 | DX06811019 | Pru::HIO32 B | 96.94 | 99.04 | 101.22 |
| 1 | DX08605019 | DX06811019 | Pru::HIO32 B | 105.60 | 92.24 | 100.42 |
| 1 | DX08605020 | DX06811019 | Pru::HIO32 B | 87.79 | 113.55 | 106.14 |
| 1 | DX08605021 | DX06811019 | Pru::HIO32 B | 99.58 | 101.26 | 99.94 |
| 1 | DX08605022 | DX06811019 | Pru::HIO32 B | 90.45 | 110.46 | 105.70 |
| 1 | DX08623001 | COL-0 | None | 93.91 | 105.89 | 102.88 |
| 1 | DX08623002 | COL-0 | None | 100.08 | 99.99 | 103.70 |
| 1 | DX08623003 | COL-0 | None | 108.71 | 92.86 | 94.25 |
| 1 | DX08623004 | COL-0 | None | 95.84 | 107.12 | 101.81 |
| 1 | DX08623005 | COL-0 | None | 109.88 | 91.18 | 95.46 |
| 1 | DX08623006 | COL-0 | None | 96.14 | 103.02 | 103.80 |
| 1 | DX08623007 | COL-0 | None | 97.90 | 102.36 | 97.97 |
| 1 | DX08623008 | COL-0 | None | 98.60 | 100.29 | 100.89 |
| 1 | DX08623009 | COL-0 | None | 94.86 | 102.34 | 106.05 |
| 1 | DX08623010 | COL-0 | None | 104.09 | 94.94 | 93.17 |
| 2 | DX08601001 | DX06811009 | Pru::HIO32 B | 107.08 | 101.44 | 97.31 |
| 2 | DX08601002 | DX06811009 | Pru::HIO32 B | 95.21 | 109.08 | 105.64 |
| 2 | DX08601003 | DX06811009 | Pru::HIO32 B | 99.01 | 101.81 | 101.15 |
| 2 | DX08601004 | DX06811009 | Pru::HIO32 B | 100.00 | 107.48 | 104.95 |
| 2 | DX08601005 | DX06811009 | Pru::HIO32 B | 104.08 | 96.23 | 98.71 |
| 2 | DX08601006 | DX06811009 | Pru::HIO32 B | 89.06 | 108.24 | 108.21 |
| 2 | DX08601007 | DX06811009 | Pru::HIO32 B | 95.15 | 108.47 | 103.10 |
| 2 | DX08601008 | DX06811009 | Pru::HIO32 B | 98.38 | 105.73 | 103.04 |
| 2 | DX08601009 | DX06811009 | Pru::HIO32 B | 97.73 | 102.00 | 105.02 |
| 2 | DX08601010 | DX06811009 | Pru::HIO32 B | 102.29 | 94.15 | 100.04 |
| 2 | DX08601011 | DX06811009 | Pru::HIO32 B | 99.23 | 99.34 | 102.96 |
| 2 | DX08601012 | DX06811009 | Pru::HIO32 B | 96.64 | 104.79 | 101.60 |
| 2 | DX08601013 | DX06811009 | Pru::HIO32 B | 92.69 | 109.85 | 106.71 |
| 2 | DX08601014 | DX06811009 | Pru::HIO32 B | 90.40 | 110.30 | 105.11 |
| 2 | DX08601015 | DX06811009 | Pru::HIO32 B | 96.45 | 100.56 | 105.22 |
| 2 | DX08601016 | DX06811009 | Pru::HIO32 B | 98.01 | 101.82 | 102.62 |
| 2 | DX08601017 | DX06811009 | Pru::HIO32 B | 100.74 | 101.04 | 99.53 |
| 2 | DX08601018 | DX06811009 | Pru::HIO32 B | 97.73 | 101.50 | 99.40 |
| 2 | DX08601019 | DX06811009 | Pru::HIO32 B | 98.71 | 97.40 | 101.41 |
| 2 | DX08601020 | DX06811009 | Pru::HIO32 B | 97.32 | 108.53 | 100.50 |
| 2 | DX08601022 | DX06811009 | Pru::HIO32 B | 93.08 | 98.60 | 104.54 |
| 2 | DX08619001 | COL-0 | None | 98.59 | 103.15 | 97.33 |
| 2 | DX08619002 | COL-0 | None | 96.81 | 100.24 | 106.91 |
| 2 | DX08619003 | COL-0 | None | 106.21 | 95.25 | 98.64 |
| 2 | DX08619004 | COL-0 | None | 99.58 | 102.72 | 98.19 |
| 2 | DX08619005 | COL-0 | None | 100.73 | 103.02 | 99.10 |
| 2 | DX08619006 | COL-0 | None | 98.19 | 101.37 | 102.54 |
| 2 | DX08619007 | COL-0 | None | 102.70 | 97.42 | 99.59 |
| 2 | DX08619008 | COL-0 | None | 96.36 | 102.55 | 99.39 |
| 2 | DX08619009 | COL-0 | None | 97.07 | 98.99 | 101.92 |
| 2 | DX08619010 | COL-0 | None | 103.76 | 95.27 | 96.39 |
| 3 | DX08600001 | DX06811016 | Pru::HIO32 B | 94.51 | 107.97 | 105.48 |
| 3 | DX08600002 | DX06811016 | Pru::HIO32 B | 97.64 | 99.71 | 94.01 |
| 3 | DX08600003 | DX06811016 | Pru::HIO32 B | 94.47 | 106.40 | 105.17 |
| 3 | DX08600005 | DX06811016 | Pru::HIO32 B | 92.79 | 101.32 | 104.82 |
| 3 | DX08600006 | DX06811016 | Pru::HIO32 B | 94.01 | 111.42 | 101.29 |
| 3 | DX08600007 | DX06811016 | Pru::HIO32 B | 99.49 | 101.84 | 101.17 |
| 3 | DX08600008 | DX06811016 | Pru::HIO32 B | 90.96 | 104.48 | 105.99 |
| 3 | DX08600010 | DX06811016 | Pru::HIO32 B | 97.16 | 108.23 | 101.41 |
| 3 | DX08600011 | DX06811016 | Pru::HIO32 B | 97.49 | 96.91 | 101.92 |
| 3 | DX08600012 | DX06811016 | Pru::HIO32 B | 96.34 | 104.57 | 101.94 |
| 3 | DX08600013 | DX06811016 | Pru::HIO32 B | 91.94 | 106.34 | 105.11 |
| 3 | DX08600014 | DX06811016 | Pru::HIO32 B | 94.35 | 106.51 | 102.08 |
| 3 | DX08600015 | DX06811016 | Pru::HIO32 B | 97.63 | 98.50 | 99.64 |
| 3 | DX08600016 | DX06811016 | Pru::HIO32 B | 89.84 | 112.41 | 105.12 |
| 3 | DX08600017 | DX06811016 | Pru::HIO32 B | 94.38 | 104.66 | 104.26 |
| 3 | DX08600018 | DX06811016 | Pru::HIO32 B | 92.75 | 107.90 | 104.63 |
| 3 | DX08600019 | DX06811016 | Pru::HIO32 B | 100.58 | 96.55 | 96.69 |
| 3 | DX08600020 | DX06811016 | Pru::HIO32 B | 96.43 | 98.44 | 103.66 |
| 3 | DX08600022 | DX06811016 | Pru::HIO32 B | 93.44 | 102.17 | 104.71 |
| 3 | DX08618001 | COL-0 | None | 99.86 | 102.62 | 100.51 |
| 3 | DX08618002 | COL-0 | None | 96.32 | 103.50 | 101.30 |

TABLE 7-continued

| Experiment | Plant | Parent | Transgene | Relative Protein | Relative Oil | Relative Fiber |
|---|---|---|---|---|---|---|
| 3 | DX08618003 | COL-0 | None | 94.59 | 104.27 | 104.08 |
| 3 | DX08618004 | COL-0 | None | 101.65 | 94.37 | 101.02 |
| 3 | DX08618005 | COL-0 | None | 103.37 | 94.63 | 96.28 |
| 3 | DX08618006 | COL-0 | None | 102.18 | 98.36 | 97.07 |
| 3 | DX08618007 | COL-0 | None | 99.87 | 100.88 | 105.31 |
| 3 | DX08618008 | COL-0 | None | 100.82 | 101.37 | 97.75 |
| 3 | DX08618009 | COL-0 | None | 103.10 | 96.14 | 96.26 |
| 3 | DX08618010 | COL-0 | None | 98.24 | 103.87 | 100.41 |

It is claimed:

1. A transgenic plant, comprising a heterologous polynucleotide that encodes or is complementary to a sequence that encodes an HIO polypeptide having the amino acid sequence as set forth in SEQ ID NO: 2, or a polypeptide having an amino acid sequence at least 95% identical to the amino acid sequence as set forth in SEQ ID NO: 2, whereby the transgenic plant has an improved meal quality phenotype, relative to control plants.

2. The transgenic plant of claim 1, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

3. The transgenic plant of claim 1, wherein an improved meal quality phenotype comprises an increase in available metabolizable energy in meal produced from seeds of the transgenic plant, relative to control plants.

4. The transgenic plant of claim 3, wherein an increase in available metabolizable energy comprises an altered digestible protein, total protein and/or fiber content in the seeds of the transgenic plant.

5. The transgenic plant of claim 4, wherein the protein content is increased and/or the fiber content is decreased.

6. The transgenic plant of claim 3, wherein an increase in available metabolizable energy comprises a decreased fiber content in the seeds of the transgenic plant.

7. A plant part obtained from the plant according to claim 1.

8. The plant part of claim 7, which is a seed.

9. Meal, feed, or food produced from the seed of claim 8, wherein the meal, feed, or food comprises the heterologous polynucleotide or polypeptide.

10. A method of producing meal, comprising growing the transgenic plant of claim 1, and recovering meal from the plant, thereby producing meal.

11. The method of claim 10, wherein the meal is produced from seeds of the plant.

12. A feed, meal, grain, food, or seed from the transgenic plant of claim 1, wherein the meal, feed, or food comprises the heterologous polynucleotide or polypeptide and, wherein the feed, meal, grain, food, or seed from the transgenic plant has the improved meal quality phenotype, relative to feed, meal, grain, food, or seed from control plants.

13. The feed, meal, grain, food, or seed of claim 12, wherein the heterologous polynucleotide comprises the nucleic acid sequence as set forth in SEQ ID NO: 1.

14. The transgenic plant of claim 1, wherein the polypeptide comprises the amino acid amino acid sequence as set forth in SEQ ID NO: 2.

15. The transgenic plant of claim 1, wherein the heterologous polynucleotide comprises the nucleic acid sequence as set forth in SEQ ID NO: 1.

16. A method of producing a plant having an improved meal quality phenotype, said method comprising:
   a) introducing into progenitor cells of the plant a heterologous polynucleotide that encodes or is complementary to a sequence that encodes an HIO polypeptide having the amino acid sequence set forth in SEQ ID NO: 2, or a polypeptide having an amino acid sequence at least 95% identical to the amino acid sequence as set forth in SEQ ID NO: 2; and
   b) growing the transformed progenitor cells to produce a transgenic plant, wherein the heterologous polynucleotide is expressed, and the transgenic plant exhibits an improved meal quality phenotype relative to control plants, thereby producing the improved meal quality phenotype in the plant.

17. A plant obtained by a method of claim 16.

18. The plant of claim 17, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

19. The plant of claim 17, wherein the plant is selected from the group consisting of a plant grown from said progenitor cells, a plant that is the direct progeny of a plant grown from said progenitor cells, and a plant that is the indirect progeny of a plant grown from said progenitor cells.

20. The method of claim 16, wherein the polypeptide comprises the amino acid sequence as set forth in SEQ ID NO: 2.

21. The method of claim 16, wherein the heterologous polynucleotide comprises the nucleic acid sequence as set forth in SEQ ID NO: 1.

* * * * *